United States Patent
Arahira et al.

(10) Patent No.: US 8,367,084 B2
(45) Date of Patent: Feb. 5, 2013

(54) OILY BASE FOR A COSMETIC AND COSMETIC COMPRISING THE SAME

(75) Inventors: Nana Arahira, Narita (JP); Yuki Kokeguchi, Narita (JP); Kiyotaka Kawai, Narita (JP)

(73) Assignee: Kokyu Alcohol Kogyo Co., Ltd., Narita-shi, Chiba (JP)

( * ) Notice: Subject to any disclaimer, the term of this patent is extended or adjusted under 35 U.S.C. 154(b) by 87 days.

(21) Appl. No.: 12/802,950

(22) Filed: Jun. 17, 2010

(65) Prior Publication Data

US 2010/0324136 A1 Dec. 23, 2010

Related U.S. Application Data

(60) Provisional application No. 61/269,057, filed on Jun. 19, 2009.

(51) Int. Cl.
*A61K 8/02* (2006.01)
*A61K 8/72* (2006.01)
*A61K 8/30* (2006.01)
*A61K 31/74* (2006.01)

(52) U.S. Cl. .............. 424/401; 424/70.11; 424/70.31; 424/78.03

(58) Field of Classification Search .............. None
See application file for complete search history.

(56) References Cited

U.S. PATENT DOCUMENTS

| | | | |
|---|---|---|---|
| 5,635,165 A | 6/1997 | Panitch | |
| 2004/0241198 A1* | 12/2004 | Blin et al. .................. | 424/401 |
| 2007/0264207 A1 | 11/2007 | Tsuchikawa et al. | |
| 2010/0028277 A1* | 2/2010 | Chodorowski-Kimmes et al. .............. | 424/59 |

FOREIGN PATENT DOCUMENTS

| | | |
|---|---|---|
| JP | 50-076238 | 6/1975 |
| JP | 8-099827 | 4/1996 |
| JP | 11-514350 | 12/1999 |
| JP | 2001-342109 | 12/2001 |
| JP | 2003-041087 | 2/2003 |
| JP | 2004-262913 | 9/2004 |
| JP | 2004-277420 | 10/2004 |
| JP | 2005-036005 | 2/2005 |
| JP | 2005-112823 | 4/2005 |
| JP | 2005-336189 | 12/2005 |
| JP | 2005-350466 | 12/2005 |
| JP | 2006-188518 | 7/2006 |
| JP | 2006-241003 | 9/2006 |
| JP | 2007-176866 | 7/2007 |
| JP | 2008-162965 | 7/2008 |

OTHER PUBLICATIONS

Fragrance Journal vol. 23, No. 10, pp. 120-121, Oct. 15, 2007.
New Cosmetic Handbook, pp. 61, 62, 68-72, Oct. 30, 2006.

* cited by examiner

*Primary Examiner* — Robert A Wax
*Assistant Examiner* — Jeffrey T Palenik
(74) *Attorney, Agent, or Firm* — Jordan and Hamburg LLP

(57) ABSTRACT

The present invention provides an oily base for a cosmetic comprising an ester compound made from a multivalent alcohol and a fatty acid, characterized in that the ester compound is made from pentaerythritol and isononanoic acid and a molar ratio of a pentaerythritol residue and an isononanoic acid residue in the ester compound is 1.0:2.3 to 1.0:4.0. The oily base for a cosmetic of the present invention has proper oily feeling with moistness, no sticky feeling, excellent adhesion to the skin and safety to the skin, and excellent compatibility with oil agents, among others, silicone oil. Furthermore, upon blending the present oily base in a cosmetic, besides having proper emollient property and moisturizing property, the cosmetic exhibits smooth feeling on use, excellent adhesion to the skin and safety to the skin, excellent cosmetic effect-holding ability, and storage stability.

27 Claims, No Drawings

OILY BASE FOR A COSMETIC AND COSMETIC COMPRISING THE SAME

REFERENCE TO RELATED APPLICATION

This application claims the benefit of the filing date of Provisional Application No. 61/269,057 filed Jun. 19, 2009.

BACKGROUND OF THE INVENTION

The present invention relates to an oily base for a cosmetic comprising an ester compound made from a multivalent alcohol and a fatty acid, and a cosmetic comprising the same, more specifically to an oily base for a cosmetic comprising an ester compound made from pentaerythritol and isononanoic acid, a cosmetic comprising the same, and a process for the preparation of the said ester compound.

In the prior art, various ester compounds are known as an oily base used in various cosmetics.

Document 1[*1] discloses a lip-care and/or lip make-up cosmetic comprising polyurethane particles as a filler and less than 15% by weight of water and/or an aqueous solvent. The invention described in this document intends to give gloss or gloss-holding property to the lip-care and/or lip make-up cosmetic. Document 1 also describes that the cosmetic may comprise a fatty phase. As the fatty phase, mention is made of oil selected from polybutene, hydrogenated polyisobutylene, polydecene, hydrogenated polydecene, vinylpyrrolidone copolymer such as polyvinylpyrrolidone/hexadecene copolymer, pentaerythrityl tetrapelargonate, polyglyceryl-2 triisostearate, tridecyl trimeritate, triisoarachidyl citrate, pentaerythrityl tetraisononanoate, glyceryl triisostearate, pentaerythrityl tetraisostearate, glyceryl tris(2-decyl)tetradecanoate, phenyl silicone and vegetable oil such as sesame oil. However, among these, only polyvinylpyrrolidone/hexadecene copolymer, polybutene and phenyltrimethicone are used in the Examples, although there are described many kinds of oil including the ester compounds which may be used as the fatty phase. These kinds of oil are selected from the viewpoint of holding gloss. The oil gives gloss to the lip-care and/or lip make-up cosmetic.

Document 2[*2] discloses a keratin fiber-care or make-up cosmetic composition wherein the solid content is more than 47% by weight, which is determined according to dry solid content extract, and the consistency index is less than 1,000 Pa. The aforesaid composition may comprise at least one fatty phase containing at least one particular structuring agent. The aforesaid invention makes it possible to give the predetermined consistency to the composition and to incorporate much amount of the fatty phase into the composition by the use of the fatty phase containing the particular structuring agent. In this way, a combination of easy and even application, satisfactory feeling of volume and isolating effect has been realized. It is described that as the oil of which the fatty phase is composed, use may be made of polyisobutylene, hydrogenated polyisobutylene, polydecene, hydrogenated polydecene, an ester, oil originated from vegetables and the mixture thereof. Among these, as the ester, mention is made of a linear fatty acid ester having 30 to 70 carbon atoms such as pentaerythrityl tetrapelargonate, a hydroxyl ester such as diisostearyl malate, an aromatic ester such as tridecyl trimellitate, an ester of $C_{24}$-$C_{28}$ branched fatty acids or fatty alcohols such as triisocetyl citrate, pentaerythrityl tetraisononanoate, glyceryl triisostearate, glyceryl 2-tridecyltetradecanoate, pentaerythrityl tetraisostearate, polyglyceryl-2 tetraisostearate, pentaerythrityl 2-tetradecyltetradecanoate. However, only polybutene is used in the Examples, although there are described many kinds of oil which may be used as the fatty phase.

Document 3[*3] discloses a cosmetic composition comprising at least one ester of an alkoxylated alcohol and a carboxylic acid, and at least one nonpolar oil. In the aforesaid invention, the cosmetic composition having high degree of gloss and good comfortability is obtained using a combination of the aforesaid ester and the nonpolar oil. Document 3 also describes that the composition may comprise non-volatile oil other than the aforesaid ester and the nonpolar oil. As the non-volatile oil, mention is made of hydrocarbon type vegetable oil such as liquid triglyceride, for example, triglyceride of heptanoic acid or octanoic acid, or jojoba oil; a hydrocarbon type ester having the formula RCOOR', for example, isononyl isononanoate, oleyl erucate or 2-octyldodecyl neopentanoate; a fatty alcohol having 12 to 26 carbon atoms, for example, octyldodecanol, 2-butyloctanol, 2-hexyldecanol, 2-undecylpentadecanol or oleyl alcohol; predetermined fluoro-oil; a fatty acid having 12 to 26 carbon atoms, for example, oleic acid and the mixture thereof; high molecular mass non-volatile oil, for example, polybutylene, hydrogenated polyisobutylene, polydecene, hydrogenated polydecene and a vinylpyrrolidone copolymer; ester; silicone oil; oil originated from vegetables such as sesame oil; and the mixture thereof. As the ester, mention is made of, for example, a linear fatty acid ester such as pentaerythrityl tetrapelargonate; a hydroxylated ester such as polyglyceryl-2 triisostearate; an aromatic ester such as tridecyl trimellitate; an ester of $C_{24}$-$C_{28}$ branched fatty alcohols or fatty acids such as triisoarachidyl citrate, pentaerythrityl tetraisononanoate, glyceryl-2-tridecyl tetradecanoate, pentaerythrityl tetraisostearate, polyglyceryl-2 tetraisostearate and pentaerythrityl2-tetradecyl tetradecanoate; a diol dimer ester and polyester such as an ester of a diol dimer and a fatty acid and an ester of a diol dimer and a dioic acid. However, these many kinds of non-volatile oil are merely described as an optional component. Among these, only pentaerythrityl tetraisostearate is used in the Examples.

Document 4[*4] discloses a beauty-care composition for a keratin material and/or a make-up composition comprising i) at least one polyester obtained by esterifying at least one triglyceride of a hydroxylated carboxylic acid with an aliphatic monocarboxylic acid and then with an aliphatic dicarboxylic acid; ii) at least one oil having a molecular weight of 6,500 to 10,000 g/mol; and iii) a predetermined medium. The aforesaid invention provides the cosmetic composition, wherein the gloss is hold on and after the application, having excellent properties such as good adaptability, spreading ability, color-holding ability after the challenge, comfortability and non-migration ability; and/or a clear outline upon adhesion to a keratin material; and/or advanced color intensity by combining the aforesaid substances i), ii) and iii). In Document 4, as the oil ii), many substances are mentioned such as a lipophilic polymer, for example, polybutylene, hydrogenated polyisobutylene, polydecene, hydrogenated polydecene and a vinylpyrrolidone copolymer; an ester; silicone oil, for example, phenyl silicone; oil originated from vegetables, for example, sesame oil; and the mixture thereof. As the ester, mention is made of a linear fatty acid ester such as pentaerythrityl tetrapelargonate; a hydroxylated ester such as polyglyceryl-2 triisostearate; an aromatic ester such as tridecyl trimellitate; an ester of fatty acids or fatty alcohols such as triisoarachidyl citrate, pentaerythrityl tetraisononanoate, glyceryl triisostearate, glyceryl 2-tridecyltetradecanoate, pentaerythrityl tetraisostearate, polyglyceryl-2 tetraisostearate, pentaerythrityl 2-tetradecyltetradecanoate. However, among these, only hydrogenated polyisobutylene and polybutylene are used as the oil ii) in the Examples.

Document 5*[5] discloses a predetermined two-phase gel composition comprising a mixture of an ester compound and a polymer compound selected from the group consisting of a three block-copolymer, a star copolymer, a radial polymer, a multi-block copolymer and the mixture thereof. As the ester compound, remarkably many substances are mentioned. However, in the Examples, among these, only isopropyl myristate, octyl methoxycinnamate, propylene glycol dicaprylate/caproate, isostearyl neopentanoate and jojoba oil are used.

Document 6*[6] discloses a gel antiperspirant composition comprising an antiperspirant compound, a starch hydrolysate ester of a predetermined carboxylic acid, a predetermined gelatinizing agent, silicone and a carrier containing a hydrocarbon in predetermined amounts. The aforesaid composition may optionally comprise an aliphatic ester. The aliphatic ester is used to improve the feeling and the ease of spreading. As the aliphatic ester, remarkably many substances are mentioned. However, in the Examples, among these, only a part of the aliphatic esters such as isopropyl myristate is used.

Document 7*[7] discloses a lip cosmetic comprising aminomodified macromolecular silicone having a predetermined structure, a predetermined oil component and polybutene. As the aforesaid oil component, mention is made of diisostearyl malate, pentaerythrityl tetra(behenate/benzoate/ethylhexanoate), glyceryl diisostearate, pentaerythrityl tetraethylhexanoate, and trioctanoin. The aforesaid invention provides a lip cosmetic having gloss, and having excellent color-holding property or cosmetic-holding property and excellent application feeling or smooth feeling by the use of a combination of the aforesaid components.

Document 8*[8] discloses an oily compact cosmetic comprising a silicone-polyamide copolymer having a predetermined structure, a fluoroalkyl group containing cyclic organopolysiloxane, and ester oil of isononanoic acid and a branched alcohol and/or ester oil of 2-ethylhexannoic acid and a multivalent alcohol. In the invention described above, the use of a combination of the aforesaid substances results in an oily solid cosmetic having good feeling on use such as good cleansing property, good spreading property and no sticky feeling, having excellent uniformity and holding property of a cosmetic film, and having good storage stability. From the viewpoint of having good cleansing property and good storage stability, as the ester oil, mention is made of isononyl isononanoate, isodecyl isononanoate, isododecyl isononanoate, neopentyl glycol di2-ethylhexanoate, glyceryl tri2-ethylhexanoate, trimethylolpropane tri2-ethylhexanoate, and pentaerythrityl tetra2-ethylhexanoate.

Document 9*[9] discloses a cosmetic composition comprising at least one ester of a diol dimer and at least one $C_4$-$C_{34}$ mono- or di-carboxylic acid and at least one film forming agent in a physiologically acceptable medium. The cosmetic composition may comprise high molar mass oil. As the high molar mass oil, mention is made of a linear fatty acid ester, a hydroxylated ester, an aromatic ester, a $C_{24}$-$C_{28}$ branched fatty alcohol or fatty acid ester, silicone oil, oil originated from vegetables, and the mixture thereof. Among these, use is preferably made of polybutylene, hydrogenated polyisobutylene, polydecene, hydrogenated polydecene, a vinylpyrolidone copolymer such as PVP/hexadecene copolymer, pentaerythrityl tetrapelargonate, polyglyceryl-2 triisostearate, tridecyl trimellitate, triisoarachidyl citrate, pentaerythrityl tetraisononanoate, glyceryl triisostearate, pentaerythrityl tetraisostearate, glyceryl tris(2-decyl)tetradecanoate, phenyl silicone, sesame oil and the mixture thereof. In the Examples, among these, only hydrogenated polyisobutene is used.

Document 10*[10] discloses a cosmetic composition comprising at least one polyester obtained by esterification of an aliphatic hydroxycarboxylic acid ester having at least two hydroxyl groups and a polycarboxylic acid; and at least one hydrocarbon-type ester other than the aforesaid polyester, and comprising a cosmetically acceptable medium. The cosmetic composition may comprise high molar mass oil. As the high molar mass oil, mention is made of a linear fatty acid ester, a hydroxylated ester, an aromatic ester, a $C_{24}$-$C_{28}$ branched fatty alcohol or fatty acid ester, silicone oil, oil originated from vegetables, and the mixture thereof. Among these, use is preferably made of polybutylene, hydrogenated polyisobutylene, polydecene, hydrogenated polydecene, a vinylpyrolidone copolymer such as PVP/hexadecene copolymer, pentaerythrityl tetrapelargonate, polyglyceryl-2 triisostearate, tridecyl trimellitate, triisoarachidyl citrate, pentaerythrityl tetraisononanoate, glyceryl triisostearate, pentaerythrityl tetraisostearate, glyceryl tris(2-decyl)tetradecanoate, phenyl silicone, sesame oil and the mixture thereof. However, in the Examples, among these, only polybutylene is used.

The documents cited above are as follows:
1 Document 1: Japanese Patent Application Laid-Open 2005-336,189;
2 Document 2: Japanese Patent Application Laid-Open 2004-262,913;
3 Document 3: Japanese Patent Application Laid-Open 2006-188,518;
4 Document 4: Japanese Patent Application Laid-Open 2004-277,420;
5 Document 5: Japanese Patent Application Laid-Open 2003-41,087;
6 Document 6: Published Japanese Translation of PCT Patent Application from other countries 1999-514,350;
7 Document 7: Japanese Patent Application Laid-Open 2007-176,866;
8 Document 8: Japanese Patent Application Laid-Open 2006-241,003;
9 Document 9: Japanese Patent Application Laid-Open 2005-350,466; and
10 Document 10: Japanese Patent Application Laid-Open 2005-36,005.

SUMMARY OF THE INVENTION

The present invention provides a novel oily base for a cosmetic comprising an ester compound made from pentaerythritol and isononanoic acid, having a pentaerythrityl residue and an isononanoic acid residue in a predetermined molar ratio, and a cosmetic comprising the same.

In Documents 1 to 10 described above, mention is made of many ester compounds as those which may be used in an oily base for a cosmetic. However, the effect has been demonstrated in few of the ester compounds. In Documents 7 and 8, pentaerythrityl tetraethylhexanoate (pentaerythritol tetra2-ethylhexanoate) is mentioned together with other ester compounds having the same effects. However, pentaerythrityl tetraethylhexanoate was not demonstrated to have good adhesion to the skin and good compatibility with the other oil agents (see Comparative Preparation Example 2 mentioned below). Therefore, a cosmetic comprising pentaerythrityl tetraethylhexanoate also was not demonstrated to have good cosmetic effects (see Comparative Example 5 mentioned below). In Document 3, there is described the Example where pentaerythrityl tetraisostearate is used as the ester compound among many ester compounds mentioned having the same effects. However, pentaerythrityl tetraisostearate also was not demonstrated to have good adhesion to the skin and good compatibility with other oil agents (see Comparative Preparation Example 3 mentioned below). Then, a cosmetic comprising pentaerythrityl tetraisostearate also was not demonstrated to have good cosmetic effects (see Comparative Examples 2, 3 and 6 mentioned below). In Documents 1 to 6 and 9 to 10, as an example of many ester compounds, pentaerythrityl tetraisononanoate is mentioned. However, in any document, pentaerythrityl tetraisononanoate is mentioned merely as one example of many ester compounds on the presumption that they may be used as an oily base for a cosmetic, and is not used in the Examples. Therefore, there was neither knowledge on the adhesion to the skin and the compatibility with other oil agents of pentaerythrityl tetraisononanoate, nor knowledge on the effects of a cosmetic comprising pentaerythrityl tetraisononanoate. In addition, there was no knowledge on the functions as an oily base for a cosmetic of the ester compound made from tetrastearic acid and pentaerythritol, that is, pentaerythrityl tetraisononanoate, pentaerythrityl triisononanoate, pentaerythrityl diisononanoate, pentaerythrityl monoisononanoate and the mixture thereof.

The inventors have made investigations to obtain more excellent ester compounds that may be used as an oily base for a cosmetic, compared to the prior art ester compounds. As a result, among many raw materials for an ester known in the prior art, we have picked out pentaerythritol and isononanoic acid and have found that the ester compound obtained by reacting these compounds in a predetermined molar ratio has proper oily feeling with moistness, no uncomfortable sticky feeling, excellent adhesion to the skin and safety to the skin, and excellent compatibility with oil agents, among others, silicone oil. Furthermore, there is found that, upon blending the aforesaid ester compound in a cosmetic, besides having proper emollient property and moisturizing property, the cosmetic exhibits smooth feeling on use, excellent adhesion to the skin and safety to the skin, excellent cosmetic effect-holding property, and storage stability. It is new knowledge that an oily base for a cosmetic comprising the ester compound, which may be mixed esters, obtained by reacting pentaerythritol and isononanoic acid in the predetermined molar ratio has the various effects mentioned above.

Thus, the present invention is (1) an oily base for a cosmetic comprising an ester compound made from a multivalent alcohol and a fatty acid, characterized in that the ester compound is made from pentaerythritol and isononanoic acid and a molar ratio of a pentaerythritol residue and an isononanoic acid residue in the ester compound is 1.0:2.3 to 1.0:4.0.

As preferred embodiments of the present invention, mention may be made of:

(2) the oily base for a cosmetic according to the above (1), wherein the molar ratio of a pentaerythritol residue and an isononanoic acid residue is 1.0:2.5 to 1.0:4.0;

(3) the oily base for a cosmetic according to the above (1), wherein the molar ratio of a pentaerythritol residue and an isononanoic acid residue is 1.0:3.0 to 1.0:4.0;

(4) the oily base for a cosmetic according to any one of the above embodiments (1) to (3), wherein the ester compound includes at least one selected from the group consisting of pentaerythrityl tetraisononanoate, pentaerythrityl triisononanoate, pentaerythrityl diisononanoate and pentaerythrityl monoisononanoate;

(5) the oily base for a cosmetic according to any one of the above embodiments (1) to (3), wherein the ester compound is composed of not more than 100 parts by mass and not less than 20.0 parts by mass of pentaerythrityl tetraisononanoate, not less than 0 part by mass and not more than 55.0 parts by mass of pentaerythrityl triisononanoate, not less than 0 part by mass and not more than 30.0 parts by mass of pentaerythrityl diisononanoate, and not less than 0 part by mass and not more than 10.0 parts by mass of pentaerythrityl monoisononanoate, and wherein the total is 100 parts by mass;

(6) the oily base for a cosmetic according to any one of the above embodiments (1) to (3), wherein the ester compound is composed of not more than 100 parts by mass and not less than 22.0 parts by mass of pentaerythrityl tetraisononanoate, not less than 0 part by mass and not more than 52.0 parts by mass of pentaerythrityl triisononanoate, not less than 0 part by mass and not more than 25.0 parts by mass of pentaerythrityl diisononanoate, and not less than 0 part by mass and not more than 5.0 parts by mass of pentaerythrityl monoisononanoate, and wherein the total is 100 parts by mass;

(7) the oily base for a cosmetic according to any one of the above embodiments (1) to (3), wherein the ester compound is composed of not more than 100 parts by mass and not less than 40.0 parts by mass of pentaerythrityl tetraisononanoate, not less than 0 part by mass and not more than 45.0 parts by mass of pentaerythrityl triisononanoate, not less than 0 part by mass and not more than 15.0 parts by mass of pentaerythrityl diisononanoate, and not less than 0 part by mass and not more than 2.0 parts by mass of pentaerythrityl monoisononanoate, and wherein the total is 100 parts by mass;

(8) the oily base for a cosmetic according to any one of the above embodiments (1) to (3), wherein the ester compound includes at least two selected from the group consisting of pentaerythrityl tetraisononanoate, pentaerythrityl triisononanoate, pentaerythrityl diisononanoate and pentaerythrityl monoisononanoate;

(9) the oily base for a cosmetic according to any one of the above embodiments (1) to (3), wherein the ester compound includes a mixture of pentaerythrityl tetraisononanoate and at least one selected from the group consisting of pentaerythrityl triisononanoate, pentaerythrityl diisononanoate and pentaerythrityl monoisononanoate;

(10) the oily base for a cosmetic according to any one of the above embodiments (1) to (3), wherein the ester compound is composed of less than 100 parts by mass and not less than 20.0 parts by mass of pentaerythrityl tetraisononanoate, more than 0 part by mass and not more than 55.0 parts by mass of pentaerythrityl triisononanoate, more than 0 part by mass and not more than 30.0 parts by mass of pentaerythrityl diisononanoate, and not less than 0 part by mass and not more than 10.0 parts by mass of pentaerythrityl monoisononanoate, and wherein the total is 100 parts by mass;

(11) the oily base for a cosmetic according to any one of the above embodiments (1) to (3), wherein the ester compound is composed of less than 100 parts by mass and not less than 22.0 parts by mass of pentaerythrityl tetraisononanoate, more than 0 part by mass and not more than 52.0 parts by mass of pentaerythrityl triisononanoate, more than 0 part by mass and not more than 25.0 parts by mass of pentaerythrityl diisononanoate, and not less than 0 part by mass and not more than 5.0 parts by mass of pentaerythrityl monoisononanoate, and wherein the total is 100 parts by mass;

(12) the oily base for a cosmetic according to any one of the above embodiments (1) to (3), wherein the ester compound is composed of less than 100 parts by mass and not less than 40.0 parts by mass of pentaerythrityl tetraisononanoate, more than 0 part by mass and not more than 45.0 parts by mass of pentaerythrityl triisononanoate, more than 0 part by mass and not more than 15.0 parts by mass of pentaerythrityl diisononanoate, and not less than 0 part by mass and not more than 2.0 parts by mass of pentaerythrityl monoisononanoate, and wherein the total is 100 parts by mass;

(13) the oily base for a cosmetic according to any one of the above embodiments (1) to (12), wherein a hydroxyl value of the oily base is 0 to 160;

(14) the oily base for a cosmetic according to any one of the above embodiments (1) to (12), wherein a hydroxyl value of the oily base is 0.3 to 140;

(15) the oily base for a cosmetic according to any one of the above embodiments (1) to (12), wherein a hydroxyl value of the oily base is 0.5 to 90;

(16) the oily base for a cosmetic according to any one of the above embodiments (1) to (15), wherein a viscosity at 25 degrees C. of the oily base is 300 to 1,000 mPa·s.;

(17) the oily base for a cosmetic according to any one of the above embodiments (1) to (15), wherein a viscosity at 25 degrees C. of the oily base is 300 to 800 mPa·s.;

(18) the oily base for a cosmetic according to any one of the above embodiments (1) to (15), wherein a viscosity at 25 degrees C. of the oily base is 300 to 600 mPa·s.;

(19) the oily base for a cosmetic according to any one of the above embodiments (1) to (18), wherein a number average molecular weight of the oily base is 500 to 800;

(20) the oily base for a cosmetic according to any one of the above embodiments (1) to (18), wherein a number average molecular weight of the oily base is 520 to 780;

(21) the oily base for a cosmetic according to any one of the above embodiments (1) to (18), wherein a number average molecular weight of the oily base is 540 to 760;

(22) a cosmetic comprising the oily base for a cosmetic according to any one of the above embodiments (1) to (21);

(23) the oily base for a cosmetic according to any one of the above embodiments (1) to (21) for skin creams, hair treatments, foundations, mascaras, eye shadows, lip glosses or lipsticks.

Another invention is

(24) a process for the preparation of an ester compound for an oily base for a cosmetic by reacting a multivalent alcohol and a fatty acid, characterized in that the multivalent alcohol is pentaerythritol, the fatty acid is isononanoic acid, and a molar ratio of pentaerythritol and isononanoic acid in the reaction is 1.0:2.3 to 1.0:4.0.

As preferred embodiments of the present invention, mention may be made of:

(25) the process according to the above (24), wherein the molar ratio of pentaerythritol and isononanoic acid is 1.0:2.5 to 1.0:4.0;

(26) the process according to the above (24), wherein the molar ratio of pentaerythritol and isononanoic acid is 1.0:3.0 to 1.0:4.0.

The oily base for a cosmetic of the present invention has proper oily feeling with moistness, no uncomfortable sticky feeling, excellent adhesion to the skin and safety to the skin, and excellent compatibility with oil agents, among others, silicone oil. Furthermore, upon blending the present oily base in a cosmetic, besides having proper emollient property and moisturizing property, the cosmetic exhibits smooth feeling on use, excellent adhesion to the skin and safety to the skin, excellent cosmetic effect-holding ability, and storage stability.

DETAILED DESCRIPTION OF THE INVENTION

The ester compound contained in the oily base for a cosmetic of the present invention is made from pentaerythritol as a multivalent alcohol and isononanoic acid as a fatty acid. A molar ratio of a pentaerythritol residue and an isononanoic acid residue in the ester compound is 1.0:2.3 to 1.0:4.0, preferably 1.0:2.5 to 1.0:4.0, more preferably 1.0:3.0 to 1.0:4.0. When the molar ratio of an isononanoic acid residue is below the aforesaid lower limit, besides having uncomfortable sticky feeling, the oily base exhibits poor safety to the skin and poor compatibility with the oil agents such as silicone oil and hydrocarbon oil.

The ester compound made from pentaerythritol and isononanoic acid includes pentaerythrityl tetraisononanoate, pentaerythrityl triisononanoate, pentaerythrityl diisononanoate and pentaerythrityl monoisononanoate. The oily base for a cosmetic of the present invention comprises at least one, preferably at least two of the ester compounds mentioned above. The ester compound preferable in the present invention is composed of not more than 100 parts by mass and not less than 20.0 parts by mass of pentaerythrityl tetraisononanoate; not less than 0 part by mass and not more than 55.0 parts by mass of pentaerythrityl triisononanoate; not less than 0 part by mass and not more than 30.0 parts by mass of pentaerythrityl diisononanoate; and not less than 0 part by mass and not more than 10.0 parts by mass of pentaerythrityl monoisononanoate, wherein the total is 100 parts by mass. More preferably, the ester compound is composed of not more than 100 parts by mass and not less than 22.0 parts by mass of pentaerythrityl tetraisononanoate; not less than 0 part by mass and not more than 52.0 parts by mass of pentaerythrityl triisononanoate; not less than 0 part by mass and not more than 25.0 parts by mass of pentaerythrityl diisononanoate; and not less than 0 part by mass and not more than 5.0 parts by mass of pentaerythrityl monoisononanoate, wherein the total is 100 parts by mass. Further more preferably, the ester compound is composed of not more than 100 parts by mass and not less than 40.0 parts by mass of pentaerythrityl tetraisononanoate; not less than 0 part by mass and not more than 45.0 parts by mass of pentaerythrityl triisononanoate; not less than 0 part by mass and not more than 15.0 parts by mass of pentaerythrityl diisononanoate; and not less than 0 part by mass and not more than 2.0 parts by mass of pentaerythrityl monoisononanoate, wherein the total is 100 parts by mass.

When the present oily base comprises at least two of the ester compounds mentioned above, the ester compound preferably contains a mixture of pentaerythrityl tetraisononanoate and at least one selected from the group consisting of pentaerythrityl triisononanoate, pentaerythrityl diisononanoate and pentaerythrityl monoisononanoate. In that case, the ester compound is preferably composed of less than 100 parts by mass and not less than 20.0 parts by mass of pentaerythrityl tetraisononanoate; more than 0 part by mass and not more than 55.0 parts by mass of pentaerythrityl triisononanoate; more than 0 part by mass and not more than 30.0 parts by mass of pentaerythrityl diisononanoate; and not less than 0 part by mass and not more than 10.0 parts by mass of pentaerythrityl monoisononanoate, wherein the total is 100 parts by mass. More preferably, the ester compound is composed of less than 100 parts by mass and not less than 22.0 parts by mass of pentaerythrityl tetraisononanoate; more than 0 part by mass and not more than 52.0 parts by mass of pentaerythrityl triisononanoate; more than 0 part by mass and not more than 25.0 parts by mass of pentaerythrityl diisononanoate; and not less than 0 part by mass and not more than 5.0 parts by mass of pentaerythrityl monoisononanoate, wherein the total is 100 parts by mass. Further more preferably, the ester compound is composed of less than 100 parts by mass and not less than 40.0 parts by mass of pentaerythrityl tetraisononanoate; more than 0 part by mass and not more than 45.0 parts by mass of pentaerythrityl triisononanoate; more than 0 part by mass and not more than 15.0 parts by mass of pentaerythrityl diisononanoate; and not less than 0 part by mass and not more than 2.0 parts by mass of pentaerythrityl monoisononanoate, wherein the total is 100 parts by mass. In any case, when the content of pentaerythrityl tetraisononanoate is below the aforesaid lower limit and the content of at least one selected from the group consisting of pentaerythrityl triisononanoate, pentaerythrityl diisononanoate and pentaerythrityl monoisononanoate is beyond the aforesaid upper limit, the adhesion ability of the ester compound to the skin and the compatibility of the ester compound with other oil agents decrease, and the desired effects cannot be attained, upon blending the ester compound in various cosmetics.

The oily base for a cosmetic of the present invention may also comprise a substance generated in the preparation of the ester compound mentioned above as a by-product, in addition to the aforesaid ester compound. The aforesaid substance, which is not clearly identified, is presumed to be, for example, substances originated from raw materials, acid anhydrides, dipentaerythritol from self-condensation of pentaerythritol, polymerization products of the esters, etc. The content of these substances, which varies depending on the molar ratio of pentaerythritol and isononanoic acid used in the reaction, is preferably not more than 5% by mass in the oily base for a cosmetic. The oily base for a cosmetic of the present invention may be used without separating these by-products. Therefore, omitting operations for separation is an advantageous, compared to the case where pentaerythrityl tetraisononanoate and other esters are used after purification. As a matter of course, these by-products may be separated and removed.

The upper limit of a hydroxyl value of the oily base for a cosmetic comprising the ester compound of the present invention is preferably 160, more preferably 140, and further more preferably 90. The lower limit, which is not clearly decided, is preferably 0.3, and more preferably 0.5. When the hydroxyl value is beyond the upper limit, the compatibility with oil agents decreases, and when it is below the lower limit, moisturizing property or emollient property becomes poor.

The upper limit of a viscosity at 25 degrees C. of the oily base for a cosmetic of the present invention is preferably 1,000 mPa·s., more preferably 800 mPa·s., and further more preferably 600 mPa·s. and the lower limit is preferably 300 mPa·s. When the viscosity is beyond the upper limit, the adhesion to the skin is too strong, and, therefore, uncomfortable sticky feeling appears upon application to the skin, and when it is below the lower limit, the adhesion ability to the skin decreases. These properties are not preferable for a cosmetic.

The upper limit of a number average molecular weight of the oily base for a cosmetic of the present invention is preferably 800, more preferably 780, and further more preferably 760, and the lower limit is preferably 500, more preferably 520, and further more preferably 540. When the number average molecular weight is beyond the upper limit, uncomfortable sticky feeling appears upon application to the skin, and when it is below the lower limit, the adhesion ability to the skin decreases. These properties are not preferable for a cosmetic.

The oily base for a cosmetic of the present invention mentioned above may be used in various cosmetics such as skin creams, hair treatments, foundations, mascaras, eye shadows, lip glosses and lipsticks. The content of the oily base in the cosmetic, which depends on a kind of the cosmetic, is preferably 0.1 to 80% by mass, more preferably 0.5 to 70% by mass, and further more preferably 0.5 to 60% by mass.

The ester compound contained in the oily base for a cosmetic of the present invention may be prepared by reacting pentaerythritol and isononanoic acid in a molar ratio of 1.0:2.3 to 1.0:4.0, preferably 1.0:2.5 to 1.0:4.0, and more preferably 1.0:3.0 to 1.0:4.0. The reaction may be carried out according to the process known in the prior art.

In the following Examples, the present invention will be described in more detail, but not limited thereto.

EXAMPLES

Preparation Examples and Comparative Preparation Examples

The substances used in the Preparation Examples and the Comparative Preparation Examples were as follows, unless otherwise stated;

Pentaerythritol: Pentaerythritol, trademark, from Mitsubishi Gas Chemical Co., Inc. or Pentarit, trademark, from Koei Perstorp Co. Ltd.

Isononanoic acid: Kyowanoic-N, trademark, from Kyowa Hakkou Chemical Co. Ltd.

2-Ethylhexanoic acid: octylic acid from Kyowa Hakkou Chemical Co. Ltd.

Isostearic acid: Isostearic acid EX, trademark, from Kokyu Alcohol Kogyo Co., Ltd.

Acid value, hydroxyl value, viscosity, number average molecular weight, adhesion ability and compatibility of the ester compounds obtained in the Preparation Examples and the Comparative Preparation Examples were Determined as Follows;

Acid value: determined in accordance with "Cosmetics Raw Material Standard 18, Method for the Determination of an Acid Value".

Hydroxyl value: determined in accordance with "Cosmetics Raw Material Standard 24, Method for the Determination of a Hydroxyl Value".

Viscosity: determined by Brookfield Viscometer DV-II+ (Spindle No. 2, 12 rpm, 25 degrees C.).

Number average molecular weight: determined from distribution of molecular weight relative to polystyrene via GPC, gel permeation chromatography, under the following conditions;

Instrument: GPC-101 from Syowa Denko Co., Ltd.,
Column: two Shodex GPC KF-603,
Eluent: THF,
Temperature: 40 degrees C. in a temperature-controlled bath for column,
Flow rate: 0.5 mL/min.,
Injection volume: 100 μL, about 0.2% (weight/volume),
Solubility: completely dissolved,
Detector: Refractive Index Detector (RI).

Adhesion ability: After 0.1 g of the ester compound obtained from Preparation Examples and Comparative Preparation Examples was applied to the inner side of the upper arm, "adhesion ability" was evaluated by twenty panels. The indication of the evaluation results is as follows. When not less than 15 panels among 20 panels evaluated the compound as "good adhesion ability", it was rated as "G". When from 6 to 9 panels evaluated the compound as "good adhesion ability", it was rated as "M". When not more than five panels evaluated the cosmetic as "good adhesion ability", it was rated as "B".

Compatibility: The oil agents used were as follows:

Hydrocarbon oil: Squalane (OLIVE SQUALANE from Kokyu Alcohol Kogyo Co., Ltd.)

Silicone oil: Cyclomethicone (DOWCORNING TORAY SH 245 FLUID, trademark, from Dow Corning Toray Co., Ltd.)

In 10% by mass of each oil agent indicated above were dissolved 90% by mass of the ester compound obtained from Preparation Examples and Comparative Preparation Examples in a hot water bath at a temperature of 80 to 90 degrees C. for 60 minutes under stirring. Next, the mixture obtained was cooled to 50 degrees C. under stirring and then placed in a temperature-controlled room at 25 degrees C. The appearance after one week was evaluated visually. The indication of the evaluation results is as follows. When the compound exhibits the compatibility with both the hydrocarbon oil and silicone oil, it was rated as "G". When the compound exhibits the compatibility with either of the two, it was rated as "M". When the compound exhibits the compatibility with neither of the two, it was rated as "B".

The quantitative analysis of each substance contained in the ester compound obtained from Preparation Examples 1 to 4 and Comparative Preparation Example 1 were carried out with a gas-chromatograph, 6890N, trademark, from Agilent Technologies, Inc.:

Instrument: Agilent Technologies 6890N;
Column: Open-tube column, DB-1, with a size of 15 m×0.25 mm×0.1 mm;
Carrier gas: helium at a flow rate of 45 ml/min.;
Oven temperature: raised from 150 to 280 degrees C. in a rate of 5 degrees C./min., and hold at 280 degrees C. for 10 minutes;
Injection temperature: 250 degrees C.;
Detector: hydrogen flame ionization detector (FID);
Injection volume: 1 µL, about 0.5% (weight/volume);
Eluent: cyclohexane; and
Solubility: completely dissolved.

Preparation Example 1

In a four-neck 2 L flask equipped with a stirrer, a thermometer, a gas inlet tube, and a Dean-Stark condenser with a water measuring trap were placed 204.2 g (1.5 mol) of pentaerythritol and 593.3 g (3.75 mol) of isononanoic acid. Then 0.8 g of methanesulfonic acid and 100 ml of toluene as a solvent were added. Next, the temperature was raised gradually to the range of 200-230 degrees C. under a flow of nitrogen gas in a rate of 20 mL/min. At the aforesaid temperature range, the reaction took place while distilling off the produced water with the solvent azeotropically. When the distillation-off water stopped, the reaction was terminated. After the temperature was lowered to 170 degrees C., the pressure was reduced to about 20 mmHg to remove the solvent, toluene, completely. 647.5 g of the ester compound, which was pale yellow and viscous, was obtained.

Preparation Example 2

The procedures of Preparation Example 1 were repeated, except that the amount of isononanoic acid was changed to 711.9 g (4.5 mol). 706.2 g of the ester compound, which was pale yellow and viscous, was obtained.

Preparation Example 3

The procedures of Preparation Example 1 were repeated, except that the amount of isononanoic acid was changed to 830.6 g (5.25 mol). 843.5 g of the ester compound, which was pale yellow and viscous, was obtained.

Preparation Example 4

The procedures of Preparation Example 1 were repeated, except that the amount of isononanoic acid was changed to 949.2 g (6.0 mol). 964.2 g of the ester compound, which was pale yellow and viscous, was obtained.

Comparative Preparation Example 1

The procedures of Preparation Example 1 were repeated, except that the amount of isononanoic acid was changed to 474.6 g (3.0 mol). 503.5 g of the ester compound, which was pale yellow and viscous, was obtained.

Comparative Preparation Example 2

The procedures of Preparation Example 1 were repeated, except that 864.6 g (6.0 mol) of 2-ethylhexanoic acid was used in place of isononanoic acid. 896.2 g of the ester compound, which was pale yellow and viscous, was obtained.

Comparative Preparation Example 3

The procedures of Preparation Example 1 were repeated, except that 1707 g (6.0 mol) of isostearic acid was used in place of isononanoic acid. 1726 g of the ester compound, which was pale yellow and viscous, was obtained.

Composition and properties of each product obtained in the Preparation Examples and the Comparative Preparation Examples are shown in Table 1.

TABLE 1

| | Molar ratio in the reaction | | Composition of the product in % by mass *3 | | | | | Acid value | Hydroxyl value | Viscosity in mPa · s at 25° C. | Number average molecular weight | Adhesion ability | Compatibility |
|---|---|---|---|---|---|---|---|---|---|---|---|---|---|
| | penta-erythritol | isononanoic acid | mono-ester | di-ester | tri-ester | tetra-ester | other compound | | | | | | |
| Prep. Ex. 1 | 1.0 | 2.5 | 2.0 | 21.3 | 49.5 | 25.1 | 2.1 | 0.02 | 131.52 | 700 | 540 | G | M |

TABLE 1-continued

|  | Molar ratio in the reaction | | Composition of the product in % by mass *3 | | | | | Acid value | Hydroxyl value | Viscosity in mPa·s at 25° C. | Number average molecular weight | Adhesion ability | Compatibility |
|---|---|---|---|---|---|---|---|---|---|---|---|---|---|
|  | penta-erythritol | isononanoic acid | mono-ester | di-ester | tri-ester | tetra-ester | other compound | | | | | | |
| Prep. Ex. 2 | 1.0 | 3.0 | 0.9 | 8.8 | 42.2 | 43.9 | 4.2 | 0.02 | 82.29 | 490 | 590 | G | G |
| Prep. Ex. 3 | 1.0 | 3.5 | 0.4 | 1.3 | 27.3 | 66.6 | 4.4 | 0.03 | 36.27 | 380 | 670 | G | G |
| Prep. Ex. 4 | 1.0 | 4.0 | — | 0.4 | 0.3 | 97.4 | 1.9 | 0.02 | 0.51 | 320 | 730 | G | G |
| Com. Prep. Ex. 1 | 1.0 | 2.0 | 12.6 | 33.8 | 37.1 | 11.9 | 4.6 | 0.5 | 227.91 | 1200 | 470 | B | B |
| Com. Prep. Ex. 2 | 1.0 | 4.0 *1 | — | — | — | — | — | 0.02 | 1.25 | 109 | 640 | B | M |
| Com. Prep. Ex. 3 | 1.0 | 4.0 *2 | — | — | — | — | — | 0.38 | 0.59 | 290 | 1200 | M | M |

In Table 1,
*1 and *2 2-ethylhexanoic acid and isostearic acid were used respectively in place of isononanoic acid.
*3 the mono-ester, the di-ester, the tri-ester and the tetra-ester in the composition of the product correspond to pentaerythrityl monoisononanoate, pentaerythrityl diisononanoate, pentaerythrityl triisononanoate and pentaerythrityl tetraisononanoate, respectively.

The molar ratio of isononanoic acid in the ester-preparation reaction is varied within the present invention in Preparation Examples 1 to 4. The ester compound was obtained as a mixture of pentaerythrityl monoisononanoate, pentaerythrityl diisononanoate, pentaerythrityl triisononanoate and pentaerythrityl tetraisononanoate in Preparation Examples 1 to 3, and as a mixture of pentaerythrityl diisononanoate, pentaerythrityl triisononanoate and pentaerythrityl tetraisononanoate in Preparation Example 4. In either mixture, the molar ratio of a pentaerythritol residue and an isononanoic acid residue was within the present invention. The adhesion to the skin was good in any ester compound obtained. In addition, the compatibility with the oil agents was good. The viscosity of the ester compound obtained tends to increase with the increase of the molar ratio of isononanoic acid, i.e. the molar ratio of an isononanoic acid residue. In any ester compound, the viscosity was proper as an oil base for a cosmetic.

Meanwhile, in Comparative Preparation Example 1, the molar ratio of isononanoic acid was less than the lower limit in the present invention. The ester compound was obtained as a mixture of pentaerythrityl monoisononanoate, pentaerythrityl diisononanoate, pentaerythrityl triisononanoate and pentaerythrityl tetraisononanoate. The molar ratio of an isononanoic acid residue to a pentaerythritol residue was less than the lower limit in the present invention. The viscosity of the ester compound obtained was extremely high, and the adhesion ability, the compatibility and the safety to the skin were poor. In Comparative Preparation Example 2, 2-ethylhexanoic acid was used in place of isononanoic acid in Preparation Example 1. The adhesion to the skin was poor, and the compatibility with the oil agents was not good. In Comparative Preparation Example 3, isostearic acid was used in place of isononanoic acid in Preparation Example 1. Both the adhesion to the skin and the compatibility with the oil agents were not good.

Examples and Comparative Examples

The substances used in the following Examples and Comparative Examples are as follows, unless otherwise stated:
Squalane: OLIVE SQUALANE from Kokyu Alcohol Kogyo Co., Ltd.;
Polyglyceryl-2 isostearate/dimer dilinoleate copolymer: from Kokyu Alcohol Kogyo Co., Ltd., HAILUCENT ISDA, trademark;
Polyglyceryl-10 stearate: from Nikko Chemicals Co., Ltd., NIKKOL Decaglyn1-SV, trademark;
Polysorbate-80: from Kao Corporation, RHEODOL TW-0120V, trademark;
Hydrogenated lecithin: from Nikko Chemicals Co., Ltd., NIKKOL Lecinol S-10EX, trademark;
Behenyl alcohol: from Kokyu Alcohol Kogyo Co., Ltd., BEHENYL ALCOHOL 65, trademark;
Hydrogenated rapeseed oil alcohol: from Kokyu Alcohol Kogyo Co., Ltd., ALCOHOL No. 20-B, trademark;
CETEARYL ALCOHOL: from Kokyu Alcohol Kogyo Co., Ltd., CETANOL NX, trademark;
Pentylene glycol: from Kokyu Alcohol Kogyo Co., Ltd., DIOL PD, trademark;
Paraffin: from Ina Trading Co., Ltd., PARAFFIN WAX SP, trademark;
Dipropylene glycol (DPG): from Kuraray Co., Ltd., DPG-RF, trademark;
1,3-Butylene glycol (1,3-BG): from Kokyu Alcohol Kogyo Co., Ltd., HAISUGARCANE BG, trademark;
Shea butter: from Kokyu Alcohol Kogyo Co., Ltd., Shea butter-RF, trademark;
Dipentaerythrityl Hexahydroxystearate/Hexastearate/Hexarosinate: from Kokyu Alcohol Kogyo Co., Ltd., HAILUCENT 138DP, trademark;
Bis-ethoxydiglycol succinate: from Kokyu Alcohol Kogyo Co., Ltd., HAIAQUEOUSTER DCS, trademark;
Jojoba oil: from Kokyu Alcohol Kogyo Co., Ltd., ECOOIL RS, trademark;
Macadamia nut oil: from Nikko Chemicals Co., Ltd., NIKKOL Macadamian nut oil, trademark;
Stearyl alcohol: from Kokyu Alcohol Kogyo Co., Ltd., STEARYL ALCOHOL NX, trademark;
Stearyl trimonium chloride: from Clariant, Genamin STAC, trademark;
Distearyl dimonium chloride: from Clariant, Genamin DSAC, trademark;
Behen trimonium chloride: from Clariant, Genamin KDM-P, trademark;

Dicoco dimonium chloride: from Takemoto Oil & Fat Co., Ltd., Pionin B-2211, trademark;

Amodimethicone: from Dow Corning Toray Co., Ltd., SF 8452 C, trademark;

Cyclomethicone: from Dow Corning Toray Co., Ltd., SH245 Fluid, trademark;

Dimethicone: from GE Toshiba Silicone Co., Ltd., TSF451-100A, trademark, used in Examples 3 to 5;

Dimethicone: from Momentive Performance Materials Japan Co., Ltd., TSF451-10A, trademark, used in Example 9;

Phenoxy ethanol: from Toho Chemical Industry Co., Ltd., Hisolve EPH, trademark;

Mica: from Merk & Co., Inc., Timiron Star Luster MP-1001, trademark;

$TiO_2$ coated mica: from Merk & Co., Inc., Timiron Star Luster MP-115, trademark;

Silicone treated barium sulfate: from Sakai Chemical Industry Co. Ltd., platy barium sulfate H series, trademark;

Boron nitride: from Mizushima Ferroalloy Co. Ltd., Boron Nitride SHP-6, trademark;

Spherical PMMA powder: from Sekisui Plastics Co., Ltd., MBX-8C, trademark;

Talc: from US Cosmetic Corporation, Soft Talc, trademark;

Nylon powder: from Dow Corning Toray Co., Ltd., Nylon powder-TR-1, trademark;

Silicone treated microparticles of titanium oxide: from TAYCA Corporation, SMT-100SAS, trademark;

Silicone treated microparticles of zinc oxide: from TAYCA Corporation, MZ-505S, trademark;

Silicone treated titanium oxide: from US Cosmetic Corporation, DHL-TRI-77891, trademark;

Silicone treated iron oxide yellow: from US Cosmetic Corporation, DHL-Y-77492, trademark;

Silicone treated iron oxide red: from US Cosmetic Corporation, DHL-R-77491, trademark;

Silicone treated iron oxide black: from US Cosmetic Corporation, DHL-B-77499, trademark;

Dimethicone: from Momentive Performance Materials Japan Co., Ltd., TSF451-10A, trademark;

Triethylhexanoin: from Kokyu Alcohol Kogyo Co., Ltd., TOG;

Neopentyl Glycol diisononanoate: from Kokyu Alcohol Kogyo Co., Ltd., NPDIN;

Ethylhexyl methoxycinnamate: from ISP Corporation, ESCALOL 557, trademark;

Tocopherol: from Eisai Co., Ltd., E-mix D, trademark;

Hexyldecyl isostearate: from Kokyu Alcohol Kogyo Co. Ltd., ICIS;

Neopentyl Glycol diethylhexanoate: from Kokyu Alcohol Kogyo Co., Ltd., KAK NDO, trademark;

Diglycerin/Dilinoleic Acid/Hydroxystearic Acid Copolymer: from Kokyu Alcohol Kogyo Co., Ltd., RISOCAST HSDA, trademark;

Sorbitan monoisostearate: from Nihon Emulsion Co., Ltd., EMALEX SPIS-100, trademark;

Dimethicone copolyol: from Evonik Goldschmidt GmbH, ABIL EM90, trademark;

Dextrin palmitate: from Chiba Flour Milling Co., Ltd., Rheopearl KL2, trademark;

Dextrin (palmitate/ethylhexanoate): from Chiba Flour Milling Co., Ltd., Rheopearl TT2, trademark;

Microcrystalline wax: from Nikko Rica Corporation, purified microcrystalline wax;

Hydrophobicated titanium oxide: from US Cosmetic Corporation, NHS-TRI-77891, trademark;

Hydrophobicated iron oxide yellow: from US Cosmetic Corporation, NHS-Y-77492, trademark;

Hydrophobicated iron oxide red: from US Cosmetic Corporation, NHS-R-77491, trademark;

Hydrophobicated iron oxide black: from US Cosmetic Corporation, NHS-B-77499, trademark;

Nylon-6: from Ube Industries, Ltd., POMP605, trademark;

Crosslinked type silicone powder: from Dow Corning Toray Co., Ltd., Torefil E506C, trademark;

Mineral oil: from Kaneda Co., Ltd., HICALL K230, trademark;

Isostearyl isostearate: from Kokyu Alcohol Kogyo Co., Ltd., ISIS;

Isocetyl myristate: from Kokyu Alcohol Kogyo Co., Ltd., ICM-R, trademark;

Octyldodecyl neodecanoate: from Kokyu Alcohol Kogyo Co., Ltd., NEOLIGHT 2000, trademark;

Decamethylcyclopentanesiloxane: from Dow Corning Toray Co., Ltd., SH245 Fluid, trademark;

Hydrogenated castor oil Dimer dilinoleate: from Kokyu Alcohol Kogyo Co., Ltd., RISOCAST DA-L, trademark;

Candelilla wax: from STRAHL & PITSCH Inc., CANDELILLA WAX 75, trademark;

Carnauba wax: from STRAHL & PITSCH Inc., CARNAUBA WAX 142, trademark;

Beeswax: from Miki Chemical Industry & Co., Ltd., purified beeswax;

Polyethylene: from Baker Petrolite, Polywax 500, trademark;

Blue No. 1: from KISHI KASEI CO., LTD., Blue No. 1;

Diisostearyl malate: from Kokyu Alcohol Kogyo Co., Ltd., HAIMALATE DIS, trademark;

Glyceryl stearate (SE): from Nihon Emulsion Co., Ltd., EMALEX GMS-195, trademark;

Hydrophobicated ultramarine: from Whittaker Clark & Daniels Inc., 7104 Ultramarine Blue, trademark;

$TiO_2$ coated mica: from Merk & Co., Inc., Timiron Star Luster MP-115, trademark;

Hydrogenated polyisobutene: from NOF Corporation, PARLEAM18, trademark;

Polyglyceryl-2 diisostearate: from Kokyu Alcohol Kogyo Co., Ltd., RISOREX PGIS22, trademark;

Polyglyceryl-2 triisostearate: from Kokyu Alcohol Kogyo Co., Ltd., RISOREX PGIS23, trademark;

Pentaerythrityl tetraisostearate: from Kokyu Alcohol Kogyo Co., Ltd., KAK PTI, trademark;

Ethylhexyl hydroxystearate: from Kokyu Alcohol Kogyo Co. Ltd., RISOCAST IOHS, trademark;

Octyldodecyl stearoyloxystearate: from Kokyu Alcohol Kogyo Co., Ltd., RISOCAST ODSHS, trademark;

Octyldodecanol: from Kokyu Alcohol Kogyo Co., Ltd., RISONOL 20SP, trademark;

Inulin stearate: from Chiba Flour Milling Co., Ltd., Rheopearl ISL2, trademark;

Glyceryl (behenate/eicosanedioate): from The Nisshin Oillio Group, Ltd., NOMCORT HK-G, trademark;

Di(C20-40) alkyl dimer-dilinoleate: from Koster Keunen Inc., Kester Wax K82-D, trademark;

Dibutyllauroylglutamide: from Ajinomoto Co., Inc., GP-1, trademark;

Stearyldimethicone: from Clariant, Silcare Silicone 41M65, trademark;

Amide terminated polyamide resin: from Arizona Chemical, Sylvaclear 200V, trademark;

Ester terminated polyamide resin: from Arizona Chemical, Uniclear 100VG, trademark;

Red No. 218: from KISHI KASEI CO., LTD., red No. 218;
Red No. 226: from KISHI KASEI CO., LTD., red No. 226;
Red No. 201: from KISHI KASEI CO., LTD., red No. 201;
Red No. 202: from KISHI KASEI CO., LTD., red No. 202;
Carmine: from Merk & Co., Inc., COLORONA CARMINE RED, trademark;
Titanium oxide: from Ishihara Sangyo Kaisha, Ltd., Tipaque CR-30, trademark;
Synthetic Fluorphlogopite, titanium oxide, iron oxide (lame luster): from Topy Industries, Ltd., Prominence RYH, trademark;
Borosilicic acid (Ca/Al), silica, titanium oxide, stannous oxide (lame luster): from Merk & Co., Inc., Ronastar Silver, trademark;
(PET/polymethylmethacrylate) laminate (lame luster): from Daiya Chemco, Ilidescent Glitter IF8101, trademark;
Trimethylolpropane triethylhexanoate: from Kokyu Alcohol Kogyo Co., Ltd., KAK TTO, trademark;
Isotridecyl isononanoate: from Kokyu Alcohol Kogyo Co., Ltd., KAK 139, trademark;
Hydrogenated castor oil isostearate, from Kokyu Alcohol Kogyo Co., Ltd., RISOCAST MIS, trademark;
Caprylic/Capric Triglyceride: from Kokyu Alcohol Kogyo Co., Ltd., TCG-M, trademark;
Isostearyl neopentanoate: from Kokyu Alcohol Kogyo Co., Ltd., NEOLIGHT 180P, trademark;
Neopentyl Glycol dicaprate: from Kokyu Alcohol Kogyo Co., Ltd., NPDC, trademark;
Ceresin: from STRAHL & PITSCH Inc., Ceresin SP1020, trademark;
Synthetic wax, (ethylene/propylene) copolymer: from Nihon Natural Products, LIPWAX PZ80-20, trademark;
Yellow No. 4 Aluminum Lake: from KISHI KASEI CO., LTD., Yellow No. 4 Aluminum Lake;
Bengara: from US Cosmetic Corporation, NHS-R-77491, trademark;
Blue No. 1 Aluminum Lake: from KISHI KASEI CO., LTD., Blue No. 1 Aluminum Lake;
Glycerin: from Kokyu Alcohol Kogyo Co., Ltd., TRIOL VE, trademark;
(Acryloyldimethyltaurine ammonium/VP) copolymer: from Clariant, Aristoflex AVC, trademark;
Xanthan gum: from Sansho Co., Ltd., KELTROL T, trademark;
Carbomer, from Nikko Chemicals Co., Ltd., Carbopol ETD2050, trademark;
Hydroxyethyl cellulose: from Sumitomo Seika Chemicals Co., Ltd., HEC, trademark;
Hydroxypropylmethyl cellulose: from Shin-Etsu Chemical Co., Ltd., Metolose 60SH-4000, trademark;
Pentylene glycol: from Kokyu Alcohol Kogyo Co., Ltd., DIOL PD, trademark
Polyquatanium-7: from Lion Corporation, Lipoflow-MN, trademark;
Silk hydrolysate: from Seiwa Kasei Co., Ltd., Promois silk-1000Q, trademark;
Glycolic acid: from Wako Pure Chemical industries, Ltd., Glycolic acid;
Methylparaben: from Clariant, Nipagin M, trademark;
Highly polymerized methyl polysiloxane (1): from Dow Corning Toray Co., Ltd., BY 22-029, trademark.
Storage stability, applicability (ease of spreading or sliminess), oily feeling, moisturizing ability, affinity with the skin, adhesion ability and safety to the skin in each of the cosmetics prepared in the Examples and the Comparative Examples were determined as follows:

Storage Stability
Cosmetics, skin creams, hair treatments, foundations, mascaras, eye shadows, lip glosses and lipsticks, as indicated in the Examples and the Comparative Examples were prepared in accordance with the following predetermined process. Three samples were prepared per each Example. Then, two of the samples were stored in a temperature-controlled bath, one at 25 degrees C. and the other at 45 degrees C., for one month. Remaining one of the samples was maintained successively at −10 degrees C., 25 degrees C. and 45 degrees C., each for 8 hours and then successively at 45 degrees C., 25 degrees C. and −10 degrees C., each for 8 hours in a temperature-controlled room. It took 48 hours per one operation. This sequential operation was repeated 5 times. The samples thus obtained were observed in respect to deterioration of appearance (occurrence of bulky particles), coloration, smelliness and separation by organoleptic assessments. As a result, in all samples, no deterioration of appearance, no coloration and no smelliness were observed. Therefore, the evaluation of storage stability was carried out only with regard to separation. Each sample was observed visually. The indication of the evaluation results is as follows. When there was no separation in all samples, the cosmetic was rated as "G". When the sample at one of the temperatures showed separation even if it was slight, the cosmetic was rated as "M". When the samples at two or more of the temperatures showed separation, even if it was slight, the cosmetic was rated as "B".

Applicability
When each of the cosmetics obtained in the Examples and the Comparative Examples, skin creams, hair treatments, foundations, mascaras, eye shadows, lip glosses and lipsticks, was applied to the skin, "applicability" was evaluated by twenty panels. For skin creams, 0.5 g of each cosmetic was applied to the face. For hair treatments, 2.0 g were applied to the hair. For foundations, 1.0 g was applied to the face. For mascaras, 0.1 g was applied to the eye lashes. For eye shadows, 0.1 g was applied to the eyelids. For lip glosses and lipsticks, 0.2 g was applied to the lips. The indication of the evaluation results is as follows. When not less than 15 panels among 20 panels evaluated the cosmetic as "good applicability", it was rated as "G". When from 6 to 9 panels evaluated the cosmetic as "good applicability", it was rated as "M". When not more than five panels evaluated the cosmetic as "good applicability", it was rated as "B".

Oily Feeling and Moisturizing Ability
After each of the cosmetics obtained in the Examples and the Comparative Examples, skin creams, hair treatments, foundations, mascaras, eye shadows, lip glosses and lipsticks, was applied to the skin, "oily feeling and moisturizing ability" were evaluated by the same evaluation methods as in the applicability test mentioned above. That is, twenty panels were used and the same application amounts were applied to the same area of the skin. The indication of the evaluation results is as follows. When not less than 15 panels among 20 panels evaluated the cosmetic as "proper oily feeling and moisturizing ability", it was rated as "G". When from 6 to 9 panels evaluated the cosmetic as "proper oily feeling and moisturizing ability", it was rated as "M". When not more than five panels evaluated the cosmetic as "proper oily feeling and moisturizing ability", it was rated as "B".

Affinity with the Skin Such as Hair, Eye Lashes, Eyelids and Lips and Adhesion to the Skin
For each of the cosmetics obtained in the Examples and the Comparative Examples, skin creams, hair treatments, foundations, mascaras, eye shadows, lip glosses and lipsticks, "affinity with the skin such as hair, eye lashes, eyelids and lips and adhesion to the skin" were evaluated by twenty panels.

For skin creams, 0.5 g of each cosmetic was applied to the face. For hair treatments, 2.0 g were applied to the hair. For foundations, 1.0 g was applied to the face. For mascaras, 0.1 g was applied to the eye lashes. For eye shadows, 0.1 g was applied to the eyelids. For lip glosses and lipsticks, 0.2 g was applied to the lips. The indication of the evaluation results is as follows. When not less than 15 panels among 20 panels evaluated the cosmetic as "good affinity with the skin (hair, eye lashes, eyelids and lips) and good adhesion to the skin" after each cosmetic was applied to the skin, it was rated as "G". When from 6 to 9 panels evaluated the cosmetic as "good affinity with the skin (hair, eye lashes, eyelids and lips) and good adhesion to the skin" after each cosmetic was applied to the skin, it was rated as "M". When not more than five panels evaluated the cosmetic as "good affinity with the skin (hair, eye lashes, eyelids and lips) and good adhesion to the skin" after each cosmetic was applied to the skin, it was rated as "B".

Safety to the Skin

Subjects were twenty people, i.e. ten males and ten females. 0.05 g of each cosmetic obtained in the Examples or the Comparative Examples was applied to a circular patch with cotton lint of 1.0 cm diameter, which patch was applied to the forearm flexor of each subject and left for 24 hours. The patch was removed and the skin was examined 1 hour later and 24 hours later to rate the skin conditions of each subject according to the following criteria. When the results 1 hour later and 24 hours later were different, the stronger response was used for rating. When the 20 subjects exhibited (−), the rating was "G", when 1 to 2 subjects exhibited (+−) and the other subjects exhibited (−), the rating was "M"; and when three or more subjects exhibited (+−) and the other subjects exhibited (−) or when one or more subjects exhibited (+) to (+++), the rating was "B". For a hair treatment, aqueous 0.5% solution was used.

| Rating Criteria | |
| --- | --- |
| Skin Conditions | Rating |
| Erythema, edema, and blister | (+++) |
| Erythema and edema | (++) |
| Erythema | (+) |
| Slight erythema | (+−) |
| No erythema and no edema | (−) |

Examples 1 and 2

Skin Cream

Each of the compositions (A) and (B) indicated in Table 2 was separately dissolved homogenously at a temperature of 75 to 80 degrees C. Next, Composition (B) was added to Composition (A) under stirring and then emulsified with a homomixer. The emulsified mixture thus obtained was then cooled to 30 degrees C. under stirring to prepare a skin cream.

Comparative Example 1

The procedures of Example 1 were repeated, except that the ester compound obtained in Comparative Preparation Example 1 was used in place of the ester compound obtained in Preparation Example 3.

The results in Examples 1 and 2, and Comparative Example 1 are shown in Table 2. Units of all figures indicated in Table 2 and in the following tables, Tables 3 to 10, are % by mass.

TABLE 2

| | Ingredient | Ex. 1 | Ex. 2 | Com. Ex. 1 |
| --- | --- | --- | --- | --- |
| (A) | Ester compound obtained in Prep. Ex. 3 | 8.00 | — | — |
| | Ester compound obtained in Prep. Ex. 4 | — | 6.00 | — |
| | Ester compound obtained in Com. Prep. Ex. 1 | — | — | 8.00 |
| | Squalane | 7.00 | 8.00 | 7.00 |
| | Polyglyceryl-2 isostearate/dimer dilinoleate copolymer | 2.00 | — | 2.00 |
| | Polyglyceryl-10 stearate | 1.50 | — | 1.50 |
| | Polysorbate-80 | — | 1.50 | — |
| | Hydrogenated lecithin | — | 0.50 | — |
| | Behenyl alcohol | 1.00 | — | 1.00 |
| | Hydrogenated rapeseed oil alcohol | — | 3.00 | — |
| | Cetostearyl alcohol | 2.00 | — | 2.00 |
| | Pentylene glycol | 3.00 | — | 3.00 |
| | Paraffin | — | 0.50 | — |
| | Dipropylene glycol | 1.00 | — | 1.00 |
| | 1,3-Butylene glycol | — | 3.00 | — |
| | Shea butter | 4.00 | 1.00 | 4.00 |
| (B) | Glycerin | 5.00 | 3.00 | 5.00 |
| | (Acryloyldimethyltaurine ammonium/VP)copolymer | 0.25 | — | 0.25 |
| | Xanthan gum | 0.10 | 0.20 | 0.10 |
| | Carbomer | — | 0.20 | — |
| | Sodium hydroxide | — | 0.05 | — |
| | Water | 65.15 | 73.05 | 65.15 |
| | Total | 100.00 | 100.00 | 100.00 |
| Evaluation result | Storage stability | G | G | M |
| | Applicability (ease of spreading or sliminess) | G | G | B |
| | Oily feeling and moisturizing ability | G | G | B |
| | Affinity with the skin and adhesion to the skin | G | G | B |
| | Safety to the skin | G | G | M |

In Examples 1 and 2, skin creams were prepared using the ester compounds obtained in Preparation Examples 3 and 4, respectively. All the cosmetics exhibited good properties. Meanwhile, in Comparative Example 1, the ester compound obtained in Preparation Example 3 was changed to the ester compound obtained in Comparative Preparation Example 1 wherein the molar ratio of an isononanoic acid residue was below the lower limit in the present invention. The cosmetic exhibited poor properties.

Examples 3 to 5

Hair Treatment

Each of the compositions (A) and (B) indicated in Table 3 was separately dissolved homogenously at a temperature of 75 to 80 degrees C. Next, Composition (B) was added to Composition (A) under stirring and then emulsified with a homomixer. Then, Component (C) was added to the emulsified product under stirring to obtain a mixture. The mixture thus obtained was then cooled to 30 degrees C. under further stirring to prepare a hair treatment. The evaluation results are shown in Table 3.

TABLE 3

| | Ingredient | Ex. 3 | Ex. 4 | Ex. 5 |
| --- | --- | --- | --- | --- |
| (A) | Ester compound obtained in Prep. Ex. 1 | 4.50 | — | 2.80 |
| | Ester compound obtained in Prep. Ex. 2 | — | 5.00 | — |

TABLE 3-continued

| | Ingredient | Ex. 3 | Ex. 4 | Ex. 5 |
|---|---|---|---|---|
| | Ester compound obtained in Prep. Ex. 4 | — | — | 2.00 |
| | Dipentaerythrityl Hexahydroxystearate/Hexastearate/Hexarosinate | 1.00 | — | — |
| | Polyglyceryl-2 isostearate/dimer dilinoleate copolymer | — | 1.00 | — |
| | Bis-ethoxydiglycol succinate | 3.00 | — | — |
| | Jojoba oil | 1.00 | — | — |
| | Macadamia nut oil | — | 1.00 | — |
| | Stearyl alcohol | 9.00 | — | 6.00 |
| | Cetostearyl alcohol | — | 9.00 | — |
| | Behenyl alcohol | — | — | 2.00 |
| | Dipropylene glycol | 4.00 | 3.00 | 3.00 |
| | Stearyl trimonium chloride | 1.00 | — | 1.00 |
| | Distearyl dimonium chloride | — | 1.00 | 1.00 |
| | Behen trimonium chloride | — | 0.50 | — |
| | Dicoco dimonium chloride | — | 1.00 | — |
| | Amodimethicone | 0.50 | — | 0.20 |
| | Cyclomethicone | — | 1.00 | — |
| | Dimethicone | 1.00 | 2.00 | 3.00 |
| | Phenoxy ethanol | — | 0.10 | — |
| (B) | Hydroxyethyl cellulose | 0.30 | — | 0.30 |
| | Hydroxypropylmethyl cellulose | — | 0.20 | — |
| | (Acryloyldimethyltaurine | — | 0.20 | — |
| | Pentylene glycol | 3.00 | — | — |
| | Polyquatanium-7 | — | 1.00 | — |
| | Silk hydrolysate | 0.01 | — | 0.02 |
| | Glycolic acid | 1.00 | — | 1.00 |
| | Methylparaben | — | — | 0.20 |
| | Purified water | 69.29 | 74.00 | 76.48 |
| (C) | Highly polymerized methyl polysiloxane (1) | 1.40 | — | 1.00 |
| | Total | 100.00 | 100.00 | 100.00 |
| Evaluation result | Storage stability | G | G | G |
| | Applicability (ease of spreading or sliminess) | G | G | G |
| | Oily feeling and moisturizing ability | G | G | G |
| | Affinity with the skin and adhesion to the skin | G | G | G |
| | Safety to the skin | G | G | G |

In Examples 3 and 4, hair treatments were prepared using the ester compound obtained in Preparation Examples 1 and 2, respectively. And in Example 5, a hair treatment was prepared using both the ester compound obtained in Preparation Example 1 and the ester compound obtained in Preparation Example 4. All the cosmetics exhibited good properties.

Examples 6 and 7

Compact Powder Foundation

Ingredients of the composition (A) indicated in Table 4 were homogeneously dispersed with a Henschel mixer. Separately, ingredients of the composition (B) were heated to 60 degrees C. and mixed homogeneously and dissolved. Next, Composition (B) was added to Composition (A) under stirring with a Henschel mixer to disperse homogeneously. After the mixture thus obtained was cooled to 30 degrees C. and ground, it was packed into a gold plate and then was compact molded to prepare a compact powder foundation. The evaluation results are shown in Table 4.

TABLE 4

| | Ingredient | Ex. 6 | Ex. 7 |
|---|---|---|---|
| (A) | Mica | 24.00 | 21.00 |
| | TiO$_2$ coated mica | 10.00 | 11.00 |
| | Silicone treated barium sulfate | 7.00 | 8.10 |
| | Boron nitride | 2.40 | 3.00 |
| | Spherical PMMA powder | 5.00 | 4.00 |
| | Talc | 17.40 | 16.00 |
| | Nylon powder | 3.70 | 4.00 |
| | Silicone treated microparticles of titanium oxide | 5.20 | 4.00 |
| | Silicone treated microparticles of zinc oxide | 3.20 | 4.00 |
| | Silicone treated titanium oxide | 8.00 | 9.00 |
| | Silicone treated iron oxide yellow | 1.50 | 2.50 |
| | Silicone treated iron oxide red | 0.40 | 0.60 |
| | Silicone treated iron oxide black | 0.20 | 0.15 |
| (B) | Ester compound obtained in Prep. Ex. 1 | 1.00 | — |
| | Ester compound obtained in Prep. Ex. 2 | — | 2.00 |
| | Dimethicone | 3.00 | 2.00 |
| | Squalane | 1.50 | — |
| | Triethylhexanoin | 2.00 | — |
| | Neopentyl glycol diisononanoate | — | 2.00 |
| | Ethylhexyl methoxycinnamate | — | 3.00 |
| | 1,3-Butylene glycol | 4.50 | 3.00 |
| | Phenoxy ethanol | — | 0.60 |
| | Tocopherol | — | 0.05 |
| | Total | 100.00 | 100.00 |
| Evaluation result | Storage stability | G | G |
| | Applicability (ease of spreading or sliminess) | G | G |
| | Oily feeling and moisturizing ability | G | G |
| | Affinity with the skin and adhesion to the skin | G | G |
| | Safety to the skin | G | G |

In Examples 6 and 7, compact powder foundations were prepared using the ester compound obtained in Preparation Examples 1 and 2, respectively. All the cosmetics exhibited good properties.

Examples 8 to 10

W/O Type Creamy Foundation

Each of the compositions (A) and (B) indicated in Table 5 was separately dissolved homogenously at a temperature of 75 to 80 degrees C. Next, Composition (B) was added to Composition (A) under stirring and then emulsified with a homomixer. The emulsified mixture thus obtained was then cooled to 30 degrees C. under stirring to prepare a creamy foundation.

Comparative Example 2

W/O Type Creamy Foundation

The procedures of Example 10 were repeated, except that the ester compound obtained in Comparative Preparation Example 3 was used in place of the ester compound obtained in Preparation Example 4.

The results in Examples 8 to 10, and Comparative Example 2 are shown in Table 5.

TABLE 5

| | Ingredient | Ex. 8 | Ex. 9 | Ex. 10 | Com. Ex. 2 |
|---|---|---|---|---|---|
| (A) | Ester compound obtained in Prep. Ex. 2 | 10.00 | — | — | — |
| | Ester compound obtained in Prep. Ex. 3 | — | 5.50 | — | — |
| | Ester compound obtained in Prep. Ex. 4 | — | — | 19.50 | — |
| | Ester compound obtained in Com. Prep. Ex. 3 | — | — | — | 19.50 |
| | Hexyldecyl isostearate | 11.00 | — | — | — |
| | Neopentyl glycol diethylhexanoate | — | — | 3.00 | 3.00 |
| | Squalane | 5.00 | — | 1.00 | 1.00 |
| | Cyclomethicone | — | 20.00 | 5.00 | 5.00 |
| | Dimethicone | — | 2.00 | — | — |
| | Diglycerin/Dilinoleic Acid/Hydroxystearic Acid Copolymer | — | — | 1.50 | 1.50 |
| | Sorbitan monoisostearate | 1.00 | — | 1.00 | 1.00 |
| | Dimethicone copolyol | — | 1.20 | — | — |
| | Dipropylene glycol | 3.00 | — | 5.00 | 5.00 |
| | Pentylene glycol | 2.00 | 2.00 | — | — |
| | Ethanol | 2.00 | 2.00 | — | — |
| | Cetostearyl alcohol | — | 1.00 | — | — |
| | Hydrogenated rapeseed oil alcohol | — | 0.50 | — | — |
| | Dextrin palmitate | 3.00 | 2.00 | 3.00 | 3.00 |
| | Microcrystalline wax | — | 4.00 | 3.00 | 3.00 |
| | Hydrophobicated titanium oxide | 8.00 | 7.00 | 7.50 | 7.50 |
| | Hydrophobicated iron oxide yellow | 1.20 | 1.20 | 1.25 | 1.25 |
| | Hydrophobicated iron oxide red | 0.30 | 0.30 | 0.28 | 0.28 |
| | Hydrophobicated iron oxide black | 0.15 | 0.15 | 0.18 | 0.18 |
| | Talc | 1.40 | 1.35 | 2.00 | 2.00 |
| | Ethylhexyl methoxycinnamate | 1.00 | 1.00 | 1.00 | 1.00 |
| | Nylon-6 | 0.50 | — | 0.20 | 0.20 |
| | Crosslinked type silicone powder | — | 2.00 | 1.00 | 1.00 |
| (B) | Glycerin | 2.00 | 3.00 | 2.00 | 2.00 |
| | Hydroxyethyl cellulose | — | 0.30 | — | — |
| | Carbomer | — | — | 0.40 | 0.40 |
| | Sodium hydroxide | — | — | 0.15 | 0.15 |
| | Preservative | proper amount | proper amount | proper amount | proper amount |
| | Purified water | 48.45 | 43.50 | 42.04 | 42.04 |
| | Total | 100.00 | 100.00 | 100.00 | 100.00 |
| Evaluation result | Storage stability | G | G | G | M |
| | Applicability (ease of spreading or sliminess) | G | G | G | B |
| | Proper oily feeling and moisturizing ability | G | G | G | B |
| | Affinity with the skin and adhesion to the skin | G | G | G | B |
| | Safety to the skin | G | G | G | M |

In Examples 8, 9 and 10, creamy foundations were prepared using the ester compound obtained in Preparation Examples 2, 3 and 4, respectively. All the cosmetics exhibited good properties. Meanwhile, in Comparative Example 2, the ester compound obtained in Preparation Example 4, which was used in Example 10, was changed to the ester compound obtained in Comparative Preparation Example 3, i.e. pentaerythrityl tetraisostearate. The cosmetic exhibited poor properties.

Examples 11 and 12

Mascara

All the ingredients of the composition (A) other than those which were in a form of fine particles, indicated in Table 6 were dissolved homogenously at 100 degrees C. to obtain a mixture, to which the aforesaid ingredients in a form of fine particles were added to make a dispersion. Next, the dispersion was cooled to room temperature under stirring to prepare a mascara.

Comparative Example 3

Mascara

The procedures of Example 12 were repeated, except that the ester compound obtained in Comparative Preparation Example 3 was used in place of the ester compound obtained in Preparation Example 4.

The results in Examples 11 and 12, and Comparative Example 3 are shown in Table 6.

TABLE 6

| | Ingredient | Ex. 11 | Ex. 12 | Com. Ex. 3 |
|---|---|---|---|---|
| (A) | Ester compound obtained in Prep. Ex. 3 | 40.00 | — | — |
| | Ester compound obtained in Prep. Ex. 4 | — | 27.00 | — |
| | Ester compound obtained in Com. Prep. Ex. 3 | — | — | 27.00 |
| | Neopentyl glycol diisononanoate | 9.00 | 5.00 | 5.00 |
| | Mineral oil | 11.00 | 15.00 | 15.00 |
| | Neopentyl glycol diethylhexanoate | — | 4.90 | 4.90 |
| | Isostearyl isostearate | 2.00 | — | — |
| | Isocetyl myristate | 1.00 | — | — |
| | Octyldodecyl neodecanoate | 4.40 | — | — |
| | Decamethylcyclopentanesiloxane | — | 10.00 | 10.00 |
| | Polyglyceryl-2 isostearate/dimer dilinoleate copolymer | — | 2.00 | 2.00 |
| | Hydrogenated castor oil dimer dilinoleate | — | 1.00 | 1.00 |
| | Dextrin palmitate | 5.00 | — | — |
| | Dextrin (palmitate/ethylhexanoate) | — | 10.00 | 10.00 |
| | Candelilla wax | 8.00 | — | — |
| | Carnauba wax | — | 3.00 | 3.00 |

TABLE 6-continued

| | Ingredient | Ex. 11 | Ex. 12 | Com. Ex. 3 |
|---|---|---|---|---|
| | Beeswax | — | 1.00 | 1.00 |
| | Microcrystalline wax | 3.00 | — | — |
| | Polyethylene | 4.00 | 8.00 | 8.00 |
| | Hydrophobicated iron oxide black | 10.50 | 10.50 | 10.50 |
| | Hydrophobicated iron oxide red | — | 0.50 | 0.50 |
| | Blue No. 1 | 2.00 | 2.00 | 2.00 |
| | Perfume | proper amount | proper amount | proper amount |
| | Tocopherol | 0.10 | 0.10 | 0.10 |
| | Total | 100.00 | 100.00 | 100.00 |
| Evaluation result | Storage stability | G | G | B |
| | Applicability (ease of spreading or sliminess) | G | G | M |
| | Proper oily feeling and moisturizing ability | G | G | G |
| | Affinity with the skin and adhesion to the skin | G | G | B |
| | Safety to the skin | G | G | G |

In Examples 11 and 12, mascaras were prepared using the ester compound obtained in Preparation Examples 3 and 4, respectively. All the cosmetics exhibited good properties. Meanwhile, in Comparative Example 3, the ester compound obtained in Preparation Example 4, which was used in Example 12, was changed to the ester compound obtained in Comparative Preparation Example 3, i.e. pentaerythrityl tetraisostearate. The storage stability, the ease of spreading, the affinity with the skin and the adhesion to the skin were poor.

Examples 13 and 14

Eye Shadow

Each of the compositions (A) and (B) indicated in Table 7 was separately dissolved homogenously at a temperature of 75 to 80 degrees C. Next, Composition (B) was added to Composition (A) under stirring and then emulsified with a homomixer. The emulsified mixture thus obtained was then cooled to 30 degrees C. under stirring to prepare an eye shadow.

The results in Examples 13 and 14 are shown in Table 7.

TABLE 7

| | Ingredient | Ex. 13 | Ex. 14 |
|---|---|---|---|
| (A) | Ester compound obtained in Prep. Ex. 1 | 9.50 | — |
| | Ester compound obtained in Prep. Ex. 2 | — | 8.00 |
| | Hydrogenated castor oil dimer dilinoleate | 1.00 | 2.00 |

TABLE 7-continued

| | Ingredient | Ex. 13 | Ex. 14 |
|---|---|---|---|
| | Neopentyl glycol diethylhexanoate | 1.00 | — |
| | Isostearyl isostearate | — | 0.50 |
| | Triethylhexanoin | — | 0.50 |
| | Mineral oil | 1.00 | — |
| | Diisostearyl malate | 5.00 | — |
| | Glyceryl stearate(SE) | 1.50 | — |
| | Polyglyceryl-10 stearate | 1.00 | — |
| | Sorbitan monoisostearate | — | 1.00 |
| | Dextrin palmitate | 3.00 | 3.00 |
| | Hydrophobicated ultramarine | 8.20 | 8.20 |
| | Hydrophobicated iron oxide black | 1.10 | 1.10 |
| | $TiO_2$ coated mica | 1.00 | 1.00 |
| | Cyclomethicone | 5.00 | 8.00 |
| (B) | Glycerin | 2.00 | 1.50 |
| | 1,3-Butylene glycol | 2.00 | 1.50 |
| | Pentylene glycol | 3.00 | 3.00 |
| | Preservative | proper amount | proper amount |
| | Purified water | 54.70 | 60.70 |
| | Total | 100.00 | 100.00 |
| Evaluation result | Storage stability | G | G |
| | Applicability (ease of spreading or sliminess) | G | G |
| | Proper oily feeling and moisturizing ability | G | G |
| | Affinity with the skin and adhesion to the skin | G | G |
| | Safety to the skin | G | G |

In Examples 13 and 14, eye shadows were prepared using the ester compound obtained in Preparation Examples 1 and 2, respectively. All the cosmetics exhibited good properties.

Examples 15 to 18

Pasty Lip Gloss

Ingredients indicated in Table 8 were dissolved homogenously at 110 degrees C., and then defoamed. Next, the mixture thus obtained was cooled to 30 degrees C. to prepare a lip gloss.

Comparative Examples 4 and 5

Pasty Lip Gloss

The procedures of Example 15 were repeated, except that the ester compounds obtained in Comparative Preparation Examples 1 and 2 were used respectively in place of the ester compound obtained in Preparation Example 2.

The results in Examples 15 to 18, and Comparative Examples 4 and 5 are shown in Table 8.

TABLE 8

| | Example | | | | Com. Ex. | |
|---|---|---|---|---|---|---|
| Ingredient | 15 | 16 | 17 | 18 | 4 | 5 |
| Ester compound obtained in Prep. Ex. 2 | 30.00 | 40.00 | 10.00 | — | — | — |
| Ester compound obtained in Prep. Ex. 4 | — | — | — | 10.00 | — | — |
| Ester compound obtained in Com. Prep. Ex. 1 | — | — | — | — | 30.00 | — |
| Ester compound obtained in Com. Prep. Ex. 2 | — | — | — | — | — | 30.00 |
| Hydrogenated polyisobutene | — | 35.00 | 15.00 | — | — | — |
| Hydrogenated castor oil dimer dilinoleate | — | — | — | 2.00 | — | — |
| Polyglyceryl-2 isostearate/dimer dilinoleate copolymer | 40.00 | — | 25.00 | 38.00 | 40.00 | 40.00 |
| Diglycerin/Dilinoleic Acid/Hydroxystearic Acid Copolymer | — | — | 2.00 | — | — | — |
| Polyglyceryl-2 diisostearate | 10.00 | — | 10.00 | — | 10.00 | 10.00 |
| Polyglyceryl-2 triisostearate | — | 7.00 | 5.00 | 5.00 | — | — |
| Diisostearyl malate | 8.00 | 4.02 | 15.00 | 5.00 | 8.00 | 8.00 |

TABLE 8-continued

|  | Ingredient | Example | | | | Com. Ex. | |
|---|---|---|---|---|---|---|---|
|  |  | 15 | 16 | 17 | 18 | 4 | 5 |
|  | Pentaerythrityl tetraisostearate | 4.50 | — | 10.00 | 8.40 | 4.50 | 4.50 |
|  | Ethylhexyl hydroxystearate | 1.70 | 3.00 | — | 15.00 | 1.70 | 1.70 |
|  | Octyldodecyl stearoyloxystearate | — | 3.00 | 6.80 | — | — | — |
|  | Squalane | — | 2.00 | — | — | — | — |
|  | Jojoba oil | — | 2.00 | — | — | — | — |
|  | Octyldodecanol | — | — | — | 10.00 | — | — |
|  | Dextrin (palmitate/ethylhexanoate) | 3.50 | 2.00 | — | — | 3.50 | 3.50 |
|  | Inulin stearate | — | — | — | 2.00 | — | — |
|  | Glyceryl (behenate/eicosanedioate) | — | — | — | 2.00 | — | — |
|  | Di(C20-40)alkyl dimer-dilinoleate | 1.00 | — | — | — | 1.00 | 1.00 |
|  | Dibutyllauroylglutamide | — | — | 0.50 | — | — | — |
|  | Stearyldimethicone | — | 1.50 | — | — | — | — |
|  | Amide terminated polyamide resin | — | — | — | 0.50 | — | — |
|  | Ester terminated polyamide resin | — | — | — | 0.80 | — | — |
|  | Red No. 218 | — | — | — | 0.30 | — | — |
|  | Red No. 226 | 0.30 | — | — | — | 0.30 | 0.30 |
|  | Red No. 201 | — | 0.01 | — | — | — | — |
|  | Red No. 202 | — | 0.02 | — | — | — | — |
|  | Carmine | — | — | 0.30 | — | — | — |
|  | Titanium oxide | — | 0.15 | — | — | — | — |
|  | TiO2 coated mica (pearlescent agent) | 1.00 | — | — | 0.50 | 1.00 | 1.00 |
|  | Synthetic Fluorphlogopite, titanium oxide, iron oxide (lame luster) | — | 0.30 | — | — | — | — |
|  | Borosilicic acid(Ca/Al), silica, titanium oxide, stannous oxide (lame luster) | — | — | 0.40 | — | — | — |
|  | (PET/polymethylmethacrylate) laminate (lame luster) | — | — | — | 0.50 | — | — |
|  | Total | 100.00 | 100.00 | 100.00 | 100.00 | 100.00 | 100.00 |
| Evaluation result | Storage stability | G | G | G | G | B | G |
|  | Applicability (ease of spreading or sliminess) | G | G | G | G | B | M |
|  | Proper oily feeling and moisturizing ability | G | G | G | G | M | G |
|  | Affinity with the skin and adhesion to the skin | G | G | G | G | B | B |
|  | Safety to the skin | G | G | G | G | M | G |

Use was made of the ester compound obtained in Preparation Example 2 in Examples 15 to 17, and the ester compound obtained in Preparation Example 4 in Example 18 to prepare a pasty lip gloss. All the cosmetics exhibited good properties. Meanwhile, in Comparative Examples 4 and 5, the ester compound obtained in Preparation Example 2, which was used in Example 15, was changed to the ester compounds obtained in Comparative Preparation Examples 1 and 2, respectively, i.e. the ester compound where the molar ratio of an isononanoic acid residue is less than the lower limit in the present invention and pentaerythrityl tetraisostearate. In Comparative Example 4, all the properties were poor. In Comparative Example 5, the ease of spreading, the affinity with the skin and the adhesion to the skin were poor.

Examples 19 and 20

Palette Type Lip Gloss

Ingredients indicated in Table 9 were dissolved homogenously at 110 degrees C., and then defoamed. Next, the mixture thus obtained was poured into a proper mold and cooled to 30 degrees C. to prepare a lip gloss.

The results in Examples 19 and 20 are shown in Table 9.

TABLE 9

| Ingredient | Ex. 19 | Ex. 20 |
|---|---|---|
| Ester compound obtained in Prep. Ex. 3 | 25.00 | — |
| Ester compound obtained in Prep. Ex. 4 | — | 9.00 |
| Hydrogenated polyisobutene | 20.00 | — |
| Hydrogenated castor oil dimer dilinoleate | — | 5.00 |
| Diglycerin/Dilinoleic Acid/Hydroxy- | — | 1.00 |

TABLE 9-continued

| Ingredient | Ex. 19 | Ex. 20 |
|---|---|---|
| stearic Acid Copolymer | | |
| Polyglyceryl-2 isostearate/dimer dilinoleate copolymer | 10.00 | 30.00 |
| Polyglyceryl-2 diisostearate | 20.00 | 15.00 |
| Polyglyceryl-2 triisostearate | — | 15.00 |
| Diisostearyl malate | 5.00 | 10.84 |
| Pentaerythrityl tetraisostearate | 5.00 | — |
| Trimethylolpropane triethylhexanoate | — | 1.00 |
| Ethylhexyl hydroxystearate | — | 1.00 |
| Isotridecyl isononanoate | — | 4.00 |
| Octyldodecyl stearoyloxystearate | 9.25 | — |
| Squalane | — | 1.00 |
| Jojoba oil | — | 1.00 |
| Octyldodecanol | — | 1.00 |
| Dextrin (palmitate/ethylhexanoate) | — | 1.50 |
| Inulin stearate | — | 1.00 |
| Dibutyllauroylglutamide | — | 1.50 |
| Amide terminated polyamide resin | 2.00 | — |
| Ester terminated polyamide resin | 3.00 | — |
| Red No. 218 | 0.10 | — |
| Red No. 226 | 0.20 | — |
| Red No. 201 | — | 0.02 |
| Red No. 202 | — | 0.01 |
| Carmine | 0.05 | — |
| Titanium oxide | — | 0.13 |
| TiO$_2$ coated mica (pearlescent agent) | — | 1.00 |
| Synthetic Fluorphlogopite, titanium oxide, iron oxide (lame luster) | 0.10 | — |
| Borosilicic acid(Ca/Al), silica, titanium oxide, stannous oxide (lame luster) | 0.10 | — |
| (PET/polymethylmethacrylate) laminate (lame luster) | 0.20 | — |
| Total | 100.00 | 100.00 |
| Evaluation result Storage stability | G | G |
| Applicability (ease of spreading or sliminess) | G | G |

TABLE 9-continued

| Ingredient | Ex. 19 | Ex. 20 |
|---|---|---|
| Proper oily feeling and moisturizing ability | G | G |
| Affinity with the skin and adhesion to the skin | G | G |
| Safety to the skin | G | G |

In Examples 19 and 20, palette type lip glosses were prepared using the ester compound obtained in Preparation Examples 3 and 4, respectively. All the cosmetics exhibited good properties.

Examples 21 to 24

Lipstick

Ingredients indicated in Table 10 were dissolved homogenously at 110 degrees C., and then defoamed. Next, the mixture thus obtained was poured into a proper mold and cooled at 10 degrees C. for 20 minutes to prepare a lipstick.

Comparative Example 6

Lipstick

The procedures of Example 24 were repeated, except that the ester compound obtained in Comparative Preparation Example 3 was used in place of the ester compound obtained in Preparation Example 4.

The results in Examples 21 to 24, and Comparative Example 6 are shown in Table 10.

TABLE 10

| | Ingredient | Ex. 21 | Ex. 22 | Ex. 23 | Ex. 24 | Com. Ex. 6 |
|---|---|---|---|---|---|---|
| | Ester compound obtained in Prep. Ex. 1 | 10.00 | — | 33.00 | — | — |
| | Ester compound obtained in Prep. Ex. 4 | — | 15.00 | — | 22.24 | — |
| | Ester compound obtained in Com. Prep. Ex. 3 | — | — | — | — | 22.24 |
| | Hydrogenated polyisobutene | 5.00 | — | — | — | — |
| | Hydrogenated castor oil dimer dilinoleate | 20.00 | — | — | 14.00 | 14.00 |
| | Diglycerin/Dilinoleic Acid/Hydroxystearic Acid Copolymer | — | 6.00 | — | — | — |
| | Polyglyceryl-2 isostearate/dimer dilinoleate copolymer | — | — | 5.00 | 4.00 | 4.00 |
| | Dipentaerythrityl Hexahydroxystearate/Hexastearate/Hexarosinate | — | 11.00 | 10.00 | — | — |
| | Hydrogenated castor oil isostearate | — | — | 6.00 | — | — |
| | Polyglyceryl-2 diisostearate | — | 5.00 | 5.00 | — | — |
| | Polyglyceryl-2 triisostearate | 5.00 | — | 9.00 | 5.00 | 5.00 |
| | Diisostearyl malate | 10.00 | 13.50 | — | 9.00 | 9.00 |
| | Pentaerythrityl tetraisostearate | — | 8.00 | — | 9.00 | 9.00 |
| | Caprylic/Capric Triglyceride | 15.00 | 14.30 | 8.70 | 18.00 | 18.00 |
| | Ethylhexyl hydroxystearate | — | 9.60 | 2.00 | — | — |
| | Isostearyl neopentanoate | 4.00 | — | 2.00 | — | — |
| | Neopentyl glycol dicaprate | 2.00 | — | — | — | — |
| | Squalane | 1.00 | — | — | — | — |
| | Octyldodecanol | 5.00 | — | — | — | — |
| | Dextrin palmitate | — | 1.50 | — | — | — |
| | Candelilla wax | 3.00 | — | 2.00 | — | — |
| | Beeswax | — | 3.00 | 3.00 | — | — |
| | Ceresin | 5.00 | — | 1.00 | 1.00 | 1.00 |
| | Polyethylene | 5.00 | 3.00 | 5.00 | 3.00 | 3.00 |
| | Synthetic wax, (ethylene/propylene)copolymer | — | 4.00 | 2.00 | 4.00 | 4.00 |
| | Microcrystalline wax | 3.00 | 3.00 | 4.00 | 4.00 | 4.00 |
| | Yellow No. 4 Aluminum Lake | — | 0.10 | — | — | — |
| | Red No. 201 | 1.40 | — | — | — | — |
| | Red No. 202 | 1.10 | 2.00 | 1.60 | — | — |
| | Bengara | 1.20 | — | — | 0.36 | 0.36 |
| | Red No. 226 | — | — | — | 1.60 | 1.60 |
| | Blue No. 1 Aluminum Lake | — | — | 0.10 | — | — |
| | Titanium oxide | 0.80 | — | 0.10 | 1.00 | 1.00 |
| | Dimethylsilylated silica | — | 0.50 | — | 0.50 | 0.50 |
| | TiO2 coated mica (pearlescent agent) | 2.50 | — | — | 3.00 | 3.00 |
| | Synthetic Fluorphlogopite, titanium oxide, iron oxide (lame luster) | — | — | 0.10 | 0.30 | 0.30 |
| | Borosilicic acid(Ca/Al), silica, titanium oxide, stannous oxide (lame luster) | — | 0.50 | — | — | — |
| | (PET/polymethylmethacrylate) laminate (lame luster) | — | — | 0.40 | — | — |
| | Total | 100.00 | 100.00 | 100.00 | 100.00 | 100.00 |
| Evaluation result | Storage stability | G | G | G | G | G |
| | Applicability (ease of spreading or sliminess) | G | G | G | G | M |
| | Proper oily feeling and moisturizing ability | G | G | G | G | M |
| | Affinity with the skin and adhesion to the skin | G | G | G | G | M |
| | Safety to the skin | G | G | G | G | G |

In both Examples 21 and 22, lipsticks were prepared using the ester compound obtained in Preparation Example 1. In both Examples 23 and 24, lipsticks were prepared using the ester compound obtained in Preparation Example 4. All the cosmetics exhibited good properties. Meanwhile, in Comparative Example 6, the ester compound obtained in Preparation Example 4, which was used in Example 24, was changed to the ester compound obtained in Comparative Preparation Example 3, i.e. pentaerythrityl tetraisostearate. The ease of spreading, the oily feeling, the moisturizing ability, the affinity with the skin and the adhesion to the skin were not good.

The ester compound contained in an oily base for a cosmetic of the present invention is able to give not only the cosmetic effects which have not been attained by any prior art ester compounds, for example, proper emollient property and moisturizing property, but also smooth feeling on use, good adhesion to the skin, safety to the skin, good cosmetic effect-holding ability and good storage ability, to a cosmetic. Therefore, the present ester compound is useful for various cosmetics such as skin creams, hair treatments, foundations, mascaras, eye shadows, lip glosses and lipsticks.

The invention claimed is:

1. A cosmetic comprising an oily base for a cosmetic comprising ester compounds made from a multivalent alcohol and a fatty acid, the ester compounds being made from pentaerythritol and isononanoic acid and a molar ratio of a pentaerythritol residue and an isononanoic acid residue in the ester compound is 1.0:2.3 to 1.0:4.0, the ester compounds including at least two ester compounds selected from the group consisting of pentaerythrityl tetraisononanoate, pentaerythrityl triisononanoate, pentaerythrityl diisononanoate and pentaerythrityl monoisononanoate.

2. The cosmetic according to claim 1, wherein the molar ratio of a pentaerythritol residue and an isononanoic acid residue is 1.0:2.5 to 1.0:4.0.

3. The cosmetic according to claim 1, wherein the molar ratio of a pentaerythritol residue and an isononanoic acid residue is 1.0:3.0 to 1.0:4.0.

4. The cosmetic according to claim 1, wherein the ester compounds include pentaerythrityl tetraisononanoate and at least one ester compound selected from the group consisting of pentaerythrityl triisononanoate, pentaerythrityl diisononanoate and pentaerythrityl monoisononanoate.

5. The cosmetic according to claim 1, wherein the proportion of the ester compounds, in parts by mass, is:
pentaerythrityl tetraisononanoate (PTe) in an amount that is 20.0 or more and less than 100,
pentaerythrityl triisononanoate (PTr) in an amount that is more than 0 and not more than 55.0,
pentaerythrityl diisononanoate (PD) in an amount that is more than 0 and not more than 30.0, and
pentaerythrityl monoisononanoate (PM) in an amount that is not less than 0 and not more than 10.0, and wherein PTe+PTr+PD+PM=100.

6. The cosmetic according to claim 1, wherein the proportion of the ester compounds, in parts by mass, is:
pentaerythrityl tetraisononanoate (PTe) in an amount that is 22.0 or more and less than 100,
pentaerythrityl triisononanoate (PTr) in an amount that is more than 0 and not more than 52.0,
pentaerythrityl diisononanoate (PD) in an amount that is more than 0 and not more than 25.0, and
pentaerythrityl monoisononanoate (PM) in an amount that is not less than 0 and not more than 5.0, and wherein PTe+PTr+PD+PM=100.

7. The cosmetic according to claim 1, wherein the proportion of the ester compounds, in parts by mass, is:
pentaerythrityl tetraisononanoate (PTe) in an amount that is 40.0 or more and less than 100,
pentaerythrityl triisononanoate (PTr) in an amount that is more than 0 and not more than 45.0,
pentaerythrityl diisononanoate (PD) in an amount that is more than 0 and not more than 15.0, and
pentaerythrityl monoisononanoate (PM) in an amount that is not less than 0 and not more than 2.0, and wherein PTe+PTr+PD+PM100.

8. The cosmetic according to claim 1, wherein a hydroxyl value of the oily base is 0 to 160.

9. The cosmetic according to claim 1, wherein a hydroxyl value of the oily base is 0.3 to 140.

10. The cosmetic according to claim 1, wherein a hydroxyl value of the oily base is 0.5 to 90.

11. The cosmetic according to claim 1, wherein a viscosity at 25° C. of the oily base is 300 to 1,000 mPa·s.

12. The cosmetic according to claim 1, wherein a viscosity at 25° C. of the oily base is 300 to 800 mPa·s.

13. The cosmetic according to claim 1, wherein a viscosity at 25° C. of the oily base is 300 to 600 mPa·s.

14. The cosmetic according to claim 1, wherein a number average molecular weight of the oily base is 500 to 800.

15. The cosmetic according to claim 1, wherein a number average molecular weight of the oily base is 520 to 780.

16. The cosmetic according to claim 1, wherein a number average molecular weight of the oily base is 540 to 760.

17. A process for the preparation of a cosmetic, comprising preparing an ester compound for an oily base for a cosmetic comprising reacting a multivalent alcohol and a fatty acid, wherein the multivalent alcohol is pentaerythritol, the fatty acid is isononanoic acid, and a molar ratio of pentaerythritol and isononanoic acid in the reaction is 1.0:2.3 to 1.0:4.0, and admixing the ester compound with other cosmetic ingredients.

18. The process according to claim 17, wherein the molar ratio of pentaerythritol and isononanoic acid is 1.0:2.5 to 1.0:4.0.

19. The process according to claim 17, wherein the molar ratio of pentaerythritol and isononanoic acid is 1.0:3.0 to 1.0:4.0.

20. A process for the preparation of a cosmetic, comprising preparing an ester compound for an oily base for a cosmetic according to the process of claim 17 and admixing the ester compound with other cosmetic ingredients.

21. Skin creams comprising the oily base for a cosmetic according to claim 1.

22. Hair treatment comprising the oily base for a cosmetic according to claim 1.

23. Foundation comprising the oily base for a cosmetic according to claim 1.

24. Mascara comprising the oily base for a cosmetic according to claim 1.

25. Eye shadow comprising the oily base for a cosmetic according to claim 1.

26. Lip gloss comprising the oily base for a cosmetic according to claim 1.

27. Lipstick comprising the oily base for a cosmetic according to claim 1.

* * * * *